(12) United States Patent
Dror

(10) Patent No.: US 11,355,224 B2
(45) Date of Patent: Jun. 7, 2022

(54) FACILITATING PRIVACY PRESERVING JOINT MEDICAL RESEARCH

(71) Applicant: Omer Dror, Tel Aviv (IL)

(72) Inventor: Omer Dror, Tel Aviv (IL)

(73) Assignee: LYNX MD LTD, Tel Aviv (IL)

( * ) Notice: Subject to any disclaimer, the term of this patent is extended or adjusted under 35 U.S.C. 154(b) by 415 days.

(21) Appl. No.: 16/722,008

(22) Filed: Dec. 20, 2019

(65) Prior Publication Data

US 2020/0226283 A1 Jul. 16, 2020

Related U.S. Application Data

(60) Provisional application No. 62/783,819, filed on Dec. 21, 2018.

(51) Int. Cl.
| | |
|---|---|
| *G06F 21/62* | (2013.01) |
| *G16H 15/00* | (2018.01) |
| *G16H 50/70* | (2018.01) |
| *G16H 50/50* | (2018.01) |
| *G06F 16/2458* | (2019.01) |
| *G16H 30/20* | (2018.01) |
| *G16H 40/20* | (2018.01) |
| *H04L 67/10* | (2022.01) |
| *G06Q 50/26* | (2012.01) |

(52) U.S. Cl.
CPC ......... *G16H 15/00* (2018.01); *G06F 16/2462* (2019.01); *G06F 21/6227* (2013.01); *G06F 21/6245* (2013.01); *G16H 30/20* (2018.01); *G16H 40/20* (2018.01); *G16H 50/50* (2018.01); *G16H 50/70* (2018.01); *G06Q 50/265* (2013.01); *H04L 67/10* (2013.01)

(58) Field of Classification Search
None
See application file for complete search history.

(56) References Cited

U.S. PATENT DOCUMENTS

| | | | | |
|---|---|---|---|---|
| 2003/0065534 | A1* | 4/2003 | McCartney | G16H 40/20 705/2 |
| 2005/0261941 | A1* | 11/2005 | Scarlat | G16H 10/60 705/3 |
| 2014/0226888 | A1* | 8/2014 | Skidmore | G06K 9/6277 382/131 |
| 2020/0372079 | A1* | 11/2020 | De Vries | G06F 16/906 |

\* cited by examiner

*Primary Examiner* — William J. Goodchild
(74) *Attorney, Agent, or Firm* — The Roy Gross Law Firm, LLC; Roy Gross

(57) ABSTRACT

Systems and method for selectively providing information about medical data are provided. A first statistical query based on an input from a first user may be received. A first estimated property based on the first statistical query may be provided to the first user. A second statistical query based on an input from a second user may be received. A first group of users that includes the first user may be selected. It may be determined whether the first group of users includes the second user. In response to a determination that the first group of users does not include the second user, a second estimated property may be provided to the second user, and in response to a determination that the first group of users includes the second user, providing the second estimated property may be forwent.

20 Claims, 16 Drawing Sheets

820

┌─────────────────────────────────────────────────────┐
│ 822   Obtaining a privacy parameter                 │
└─────────────────────────────────────────────────────┘
                          ↓
┌─────────────────────────────────────────────────────┐
│ 824   Selecting at least one noise value based on   │
│ the obtained privacy parameter                      │
└─────────────────────────────────────────────────────┘
                          ↓
┌─────────────────────────────────────────────────────┐
│ 826   Combining the at least one noise value        │
│ with an actual property of a subgroup of a group    │
│ of patients to determine the estimated property     │
│ of the subgroup of the group of patients            │
└─────────────────────────────────────────────────────┘

┌─────────────────────────────────────────────────────┐
│ 832   After forgoing providing the first            │
│ information, receiving an indication that an        │
│ update to a status of the user occurred             │
└─────────────────────────────────────────────────────┘
                          ↓
┌─────────────────────────────────────────────────────┐
│ 834   In response to the update to the status of    │
│ the user, providing the first information           │
└─────────────────────────────────────────────────────┘

942 After providing the second estimated property of the medical data to the second user, receiving an indication that the first group of users changed to include the second user

944 In response to the received indication, providing a notification

952 In response to the second statistical query belonging to a selected group of statistical queries and the determination that the first group of users includes the second user, providing the second estimated property of the medical data to the second user

954 In response to the second statistical query not belonging to the selected group of statistical queries and the determination that the first group of users includes the second user, forgoing providing the second estimated property of the medical data to the second user

- 962 Receiving a third statistical query about the medical data, the third statistical query is based on an additional input from the first user

- 964 Determining whether the first group of users changed to include the second user

- 966 In response to a determination that the first group of users did not change to include the second user, providing a third estimated property of the medical data to the first user, the third estimated property of the medical data is based on the third statistical query

- 968 In response to a determination that the first group of users changed to include the second user, forgoing providing the third estimated property of the medical data to the first user

FIG. 9F

FACILITATING PRIVACY PRESERVING JOINT MEDICAL RESEARCH

CROSS REFERENCES TO RELATED APPLICATIONS

This application claims the benefit of priority of U.S. Provisional Patent Application No. 62/783,819, filed on Dec. 21, 2018, which is incorporated herein by reference in its entirety.

BACKGROUND

Technological Field

The disclosed embodiments generally relate to systems and methods for providing information based on medical data. More particularly, the disclosed embodiments relate to systems and methods for providing information based on private medical data.

Background Information

Numerous medical records are created, read and edited by vast number of medical care providers. Nowadays, some medical research requires access to large datasets of medical information. However, accessing medical data may prove challenging, partly due to regulatory and privacy requirements. Easing access to medical data may facilitate accelerated medical research.

SUMMARY

Embodiments consistent with the present disclosure provide systems, methods, and devices for providing information based on private medical data.

In some embodiments, systems and methods for enabling graphical illustration of private medical information are provided. In some examples, a subgroup defining input may be received, the subgroup defining input may be based on a first input from a user and may define a subgroup of a group of patients. Further, in some examples, a statistical query about the subgroup of the group of patients may be received, the statistical query may be based on a second input from the user. Further, in some examples, a size of the subgroup of the group of patients may be determined. Further, in some examples, the determined size of the subgroup of the group of patients may be compared with a selected subgroup size threshold. Further, in some examples, first information may be provided. For example, the first information may be based on the statistical query and may be configured to enable a presentation of a graphical illustration of an estimated property of the subgroup of the group of patients in response to the second input from the user. In some examples, in response to the determined size of the subgroup of the group of patients being larger than the selected subgroup size threshold, the first information may be provided, and in response to the determined size of the subgroup of the group of patients being smaller than the selected subgroup size threshold, providing the first information may be withheld and/or forwent.

In some examples, the subgroup size threshold may be randomly selected from a distribution of thresholds. In some examples, in response to the subgroup of the group of patients including a first patient, a first value for the subgroup size threshold may be selected, and in response to the subgroup of the group of patients not including the first patient, a second value for the subgroup size threshold may be selected, the second value differs from the first value. In some examples, in response to the property of the subgroup of the group of patients being of a first type, a first value for the subgroup size threshold may be selected, and in response to the property of the subgroup of the group of patients being of a second type, a second value for the subgroup size threshold may be selected, the second value differs from the first value. In some examples, the subgroup size threshold may be selected based on the user. In some examples, the subgroup size threshold may be selected based on at least one previous statistical query about the subgroup of the group of patients.

In some examples, a privacy parameter may be obtained. Further, in some examples, at least one noise value may be selected based on the obtained privacy parameter. Further, in some examples, the at least one noise value may be combined with an actual property of the subgroup of the group of patients to determine the estimated property of the subgroup of the group of patients. In some examples, in response to a first determined size of the subgroup of the group of patients, a first value for the privacy parameter may be selected, and in response to a second determined size of the subgroup of the group of patients, a second value for the privacy parameter may be selected, the second value differs from the first value. In some examples, in response to the subgroup of the group of patients including a first patient, a first value for the privacy parameter may be selected, and in response to the subgroup of the group of patients not including the first patient, a second value for the privacy parameter may be selected, the second value differs from the first value. In some examples, in response to a the property of the subgroup of the group of patients being of a first type, a first value for the privacy parameter may be selected, and in response to the property of the subgroup of the group of patients being of a second type, a second value for the privacy parameter may be selected, the second value differs from the first value. In some examples, the privacy parameter may be selected based on the user. In some examples, the privacy parameter may be selected based on at least one previous statistical query about the subgroup of the group of patients.

In some examples, for example after forgoing providing the first information, an indication that an update to a status of the user occurred may be received. Further, in some examples, in response to the update to the status of the user, the first information may be provided.

In some examples, an indication that an update to the group of patients caused an update to the subgroup defined by the subgroup defining input may be received. Further, in some examples, a size of the updated subgroup may be determined. Further, in some examples, the determined size of the updated subgroup may be compared with a selected second subgroup size threshold. Further, in some examples, second information may be provided, the second information may be based on the statistical query and configured to enable a presentation of a graphical illustration of an estimated property of the updated subgroup. In some examples, in response to the determined size of the subgroup of the group of patients being smaller than the selected subgroup size threshold and the determined size of the updated subgroup being larger than the selected second subgroup size threshold, the second information may be provided, in response to the determined size of the subgroup of the group of patients being larger than the selected subgroup size threshold, providing the second information may be withheld and/or forwent, and in response to the determined size of the updated subgroup being smaller than the selected second subgroup size threshold, providing the second information may be withheld and/or forwent.

In some examples, for example after providing the first information, an indication that an update to the group of patients caused an update to the subgroup defined by the subgroup defining input may be received. Further, in some examples, a size of the updated subgroup may be determined. Further, in some examples, the determined size of the updated subgroup may be compared with a selected second subgroup size threshold. Further, in some examples, second information may be provided, the second information may be based on the statistical query and configured to enable a presentation of a graphical illustration of an estimated property of the updated subgroup. In some examples, in response to the determined size of the subgroup of the group of patients being larger than the selected subgroup size threshold and the determined size of the updated subgroup being larger than the selected second subgroup size threshold, the second information may be provided, and in response to the determined size of the updated subgroup being smaller than the selected second subgroup size threshold, providing the second information may be withheld and/or forwent.

In some examples, for example after providing the first information, a second subgroup defining input may be received, the second subgroup defining input may be based on a third input from the user and may define a second subgroup of the group of patients. Further, in some examples, a second statistical query about the second subgroup of the group of patients may be received, the statistical query may be based on a fourth input from the user. Further, in some examples, a size of a difference between the subgroup of the group of patients and the second subgroup of the group of patients may be determined. Further, in some examples, second information may be provided, the second information may be based on the second statistical query and configured to enable a presentation of a graphical illustration of an estimated property of the second subgroup of the group of patients in response to the fourth input from the user. In some examples, in response to the determined size of the difference between the subgroup of the group of patients and the second subgroup of the group of patients being larger than a selected difference threshold, the second information may be provided, and in response to the determined size of the difference between the subgroup of the group of patients and the second subgroup of the group of patients being smaller than a selected difference threshold, providing the second information may be withheld and/or forwent.

In some examples, each patient of the subgroup of the group of patients may be associated with a medical image, and the graphical illustration may include a display of an image based on the images associated with the patients of the subgroup of the group of patients. In some examples, the graphical illustration may include a visualization of a correlation matrix between survival probabilities of patients of the subgroup of the group of patients and treatment choices associated with the patients of the subgroup of the group of patients.

In some embodiments, systems and methods for facilitating privacy preserving joint medical research are provided. For example, systems and method for selectively providing information about medical data are provided.

In some examples, a first statistical query about medical data may be received, the first statistical query may be based on an input from a first user. Further, in some examples, a first estimated property of the medical data may be provided to the first user, the first estimated property of the medical data may be based on the first statistical query. Further, in some examples, a second statistical query about the medical data may be received, the second statistical query may be based on an input from a second user (the second user may differ from the first user). Further, in some examples, a first group of users that includes the first user may be selected. Further, in some examples, it may be determined whether the first group of users includes the second user. Further, in some examples, in response to a determination that the first group of users does not include the second user, a second estimated property of the medical data may be provided to the second user (the second estimated property of the medical data may be based on the second statistical query), and in response to a determination that the first group of users includes the second user, providing the second estimated property of the medical data to the second user may be withheld and/or forwent. In some examples, the first estimated property of the medical data may be a first actual property of the medical data. In some examples, the first group of users may be selected of a plurality of alternative groups of users based on an identity of the first user. In some examples, a type of the first user may be a particular type, and the selected first group of users may include all users of the particular type from a particular plurality of users.

In some examples, a first privacy parameter may be obtained. Further, in some examples, a first at least one noise value may be selected based on the first obtained privacy parameter. Further, in some examples, the first at least one noise value may be combined with a first actual property of the medical data to determine the first estimated property of the medical data. Further, in some examples, a second privacy parameter may be obtained. Further, in some examples, a second at least one noise value may be selected based on the second obtained privacy parameter. Further, in some examples, the second at least one noise value may be combined with a second actual property of the medical data to determine the second estimated property of the medical data. In some examples, in response to the determination that the first group of users includes the second user and a first value of the obtained first privacy parameter, the second estimated property of the medical data may be provided to the second user, and in response to the determination that the first group of users includes the second user and a second value of the obtained first privacy parameter, providing the second estimated property of the medical data to the second user may be withheld and/or forwent.

In some examples, a privacy budget associated with the first group of users may be updated to reflect the providence of the first estimated property of the medical data to the first user. Further, in some examples, it may be determined whether the updated privacy budget is sufficient for the second statistical query. Further, in some examples, in response to the determination that the first group of users includes the second user and a determination that the updated privacy budget is sufficient for the second statistical query, the second estimated property of the medical data may be provided to the second user, and in response to the determination that the first group of users includes the second user and a determination that the updated privacy budget is insufficient for the second statistical query, providing the second estimated property of the medical data to the second user may be withheld and/or forwent. In some examples, for example after determining whether the updated privacy budget is sufficient for the second statistical query, a third statistical query about the medical data may be received, the third statistical query may be based on an additional input from the first user. Further, in some examples, in case the first group of users includes the second user and the second estimated property of the medical data was not provided to the second user, a third estimated property of the medical data may be provided to the first user (the third estimated property of the medical data may be based on the third statistical query), and in case the first group of users includes the second user and the second estimated property of the medical data was provided to the second user, providing the third estimated property of the medical data to the first user may be withheld and/or forwent.

In some examples, for example after determining that the first group of users does not include the second user and providing the second estimated property of the medical data to the second user, a third statistical query about the medical data may be received, the third statistical query may be based on an additional input from the first user. Further, in some examples, it may be determined whether the first group of users changed to include the second user. Further, in some examples, in response to a determination that the first group of users did not change to include the second user, a third estimated property of the medical data may be provided to the first user (the third estimated property of the medical data may be based on the third statistical query), and in response to a determination that the first group of users changed to include the second user, providing the third estimated property of the medical data to the first user may be withheld and/or forwent.

In some examples, for example after determining that the first group of users includes the second user and forgoing providing the second estimated property of the medical data to the second user, an indication that the first group of users changed to exclude the second user may be received. Further, in some examples, in response to the received indication that the first group of users changed to exclude the second user, the second estimated property of the medical data may be provided to the second user.

In some examples, for example after determining that the first group of users includes the second user and forgoing providing the second estimated property of the medical data to the second user, an indication that the first group of users changed to exclude the first user may be received. Further, in some examples, in response to the received indication that the first group of users changed to exclude the first user, the second estimated property of the medical data may be provided to the second user.

In some examples, for example after determining that the first group of users does not include the second user and providing the second estimated property of the medical data to the second user, an indication that the first group of users changed to include the second user may be received. Further, in some examples, in response to the providence of the first estimated property of the medical data to the first user, the providence of the second estimated property of the medical data to the second user, and the received indication that the first group of users changed to include the second user, a notification may be provided.

In some examples, in response to the second statistical query belonging to a selected group of statistical queries and the determination that the first group of users includes the second user, the second estimated property of the medical data may be provided to the second user, and in response to the second statistical query not belonging to the selected group of statistical queries and the determination that the first group of users includes the second user, providing the second estimated property of the medical data to the second user may be withheld and/or forwent. In some examples, the selected group of statistical queries may include a query about a total number of patients in the medical data and not include a query about a number of patients that match a particular criterion. In some examples, the selected group of statistical queries may include a query about a statistic of a particular property in the medical data of patients in a first group of patients when the size of the first group of patients is above a selected threshold, and not include the query about the statistic of the particular property in the medical data of patients in the first group of patients when the size of the first group of patients is below the selected threshold. For example, the selected threshold may be based on the particular property, may be based on the second user, and so forth.

In some examples, in response to a determination that the first group of users includes the second user, a suggestion of an alternative statistical query to be provided to the second user may be caused, the alternative statistical query may be based on the second statistical query. Further, in some examples, an indication that the second user accepted the suggested alternative statistical query may be received. Further, in some examples, in response to the received indication that the second user accepted the suggested alternative statistical query, a third estimated property of the medical data may be provided to the second user, the third estimated property of the medical data may be on the suggested alternative statistical query.

Consistent with other disclosed embodiments, a non-transitory computer readable medium may store software programs, each software program comprising data and computer implementable instructions for carrying out any of the methods described herein. For example, when the software program is executed by at least one processing device, it may be configured to perform any of the methods described herein.

The foregoing general description and the following detailed description are exemplary and explanatory only and are not restrictive of the claims.

BRIEF DESCRIPTION OF THE DRAWINGS

FIG. 8B illustrates an example of a method for determining an estimated property of a subgroup of a group of patients.

FIG. 8C illustrates an example of a method for enabling graphical illustration based on private medical information.

FIG. 9D illustrates an example of a method for selectively providing information about medical data.

FIG. 9E illustrates an example of a method for selectively providing information about medical data.

FIG. 9F illustrates an example of a method for selectively providing information about medical data.

DESCRIPTION

Figure 1:
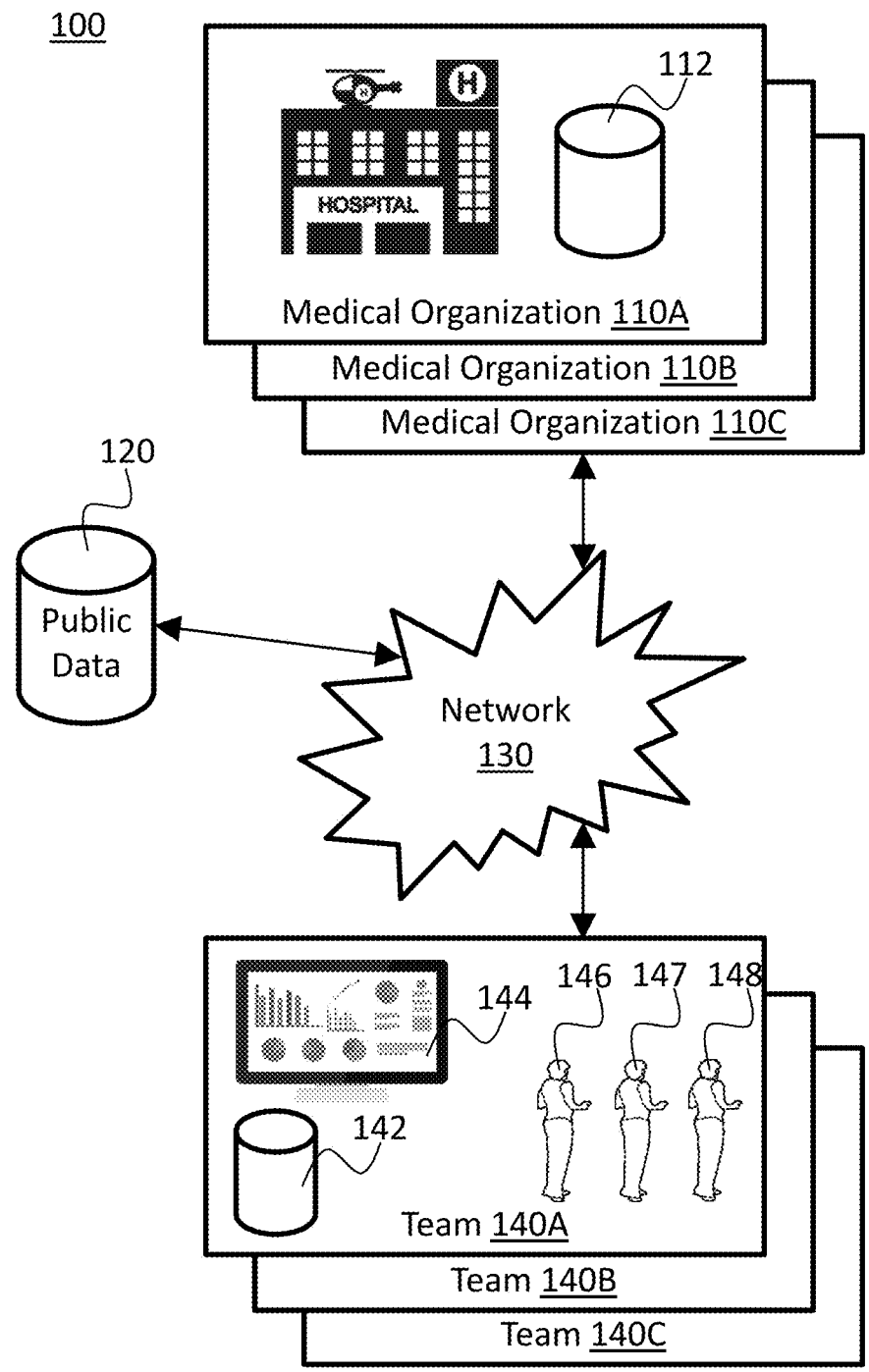
FIG. 1 is an illustration of an exemplary system for providing information based on medical data.

Unless specifically stated otherwise, as apparent from the following discussions, it is appreciated that throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include action and/or processes of a computer that manipulate and/or transform data into other data, said data represented as physical quantities, for example such as electronic quantities, and/or said data representing the physical objects. The terms "computer", "processor", "controller", "processing unit", "computing device", and "processing module" should be expansively construed to cover any kind of electronic device, component or unit with data processing capabilities, including, by way of non-limiting example, a personal computer, a wearable computer, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) may be included in at least one embodiment of the presently disclosed subject matter. Thus the appearance of the phrase "one case", "some cases", "other cases" or variants thereof does not necessarily refer to the same embodiment(s). As used herein, the term "and/or" includes any and all combinations of one or more of the associated listed items.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

It should be noted that some examples of the presently disclosed subject matter are not limited in application to the details of construction and the arrangement of the components set forth in the following description or illustrated in the drawings. The invention can be capable of other embodiments or of being practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

FIG. 1 is an illustration of an exemplary system 100 for providing information based on medical data. In some examples, system 100 may include one or more medical organizations 110 (in this example, medical organizations 110A, 110B and 110C). Some possible examples of such medical organizations 110 may include hospitals, medical clinics, medical labs, pharmacies, medical care providers 630 (described below), insurers 640 (described below), regulators 650 (described below), and so forth. Each one of the one or more medical organizations 110 may hold private medical data. In this example, medical organization 110A holds private medical data 112. Access to all or portions of private medical data 112 may be restricted, for example due to regulatory and privacy requirements, due to medical organization 110 procedures, and so forth. Some examples of such medical data 112 may include medical records 710 (described below), scheduling records 720 (described below), financial records 730 (described below), insurance records 740 (described below), research records 750 (described below), and so forth. In some examples, system 100 may include public data 120. Access to public data may be publically available to everyone. In some examples, system 100 may include one or more teams 140 (in this example, teams 140A, 140B and 140C). Some possible examples of such teams 140 may include research teams, research organizations, individual researchers, researchers 660 (described below), insurers 640 (described below), regulators 650 (described below), and so forth. In some example, each one of the one or more teams 140 may hold proprietary medical data. In this example, team 140A holds proprietary medical data 142. In some example, each one of the one or more teams 140 may use computerized data analysis devices. In this example, team 140A uses computerized data analysis device 144. Some possible implementations of computerized data analysis device 144 may include computing device 200 (described below), cloud platform 400 (described below), computational node 500 (described below), and so forth. In some example, each one of the one or more teams 140 may include one or more users. In this example, team 140A includes users 146, 147 and 148. Some possible examples of such users may include researchers 660 (described below), human data analysts, automated data analyst processes, and so forth. In some examples, data may be exchanged among elements of system 100, for example through communication network 130. Examples of communication network 130 may include the Internet, phone networks, cellular networks, satellite communication networks, private communication networks, virtual private networks (VPN), and so forth. Computerized devices (such as computing device 200, cloud platform 400, computational node 500, computerized data analysis device 144, storage devices, local storage, remote storage, network attached storage, etc.) may connect to communication network 130 directly, through local router, through wireless communication, through wired communication, and so forth.

In some examples, at least a portion of at least one of private medical data 112, public data 120 and proprietary medical data 142 may be stored in memory (such as memory 700, memory units 210, memory modules 410, etc.), in storage device (such as local storage, remote storage, network attached storage, etc.), and so forth. In some examples, at least a portion of at least one of private medical data 112, public data 120 and proprietary medical data 142 may be managed and/or controlled and/or maintained and/or collected and/or analyzed using local computing devices (such as computing device 200), local computerized servers, remote computerized servers, private and/or public cloud platforms (such as cloud platform 400), computational node (such as computational node 500), and so forth.

Figure 2A:
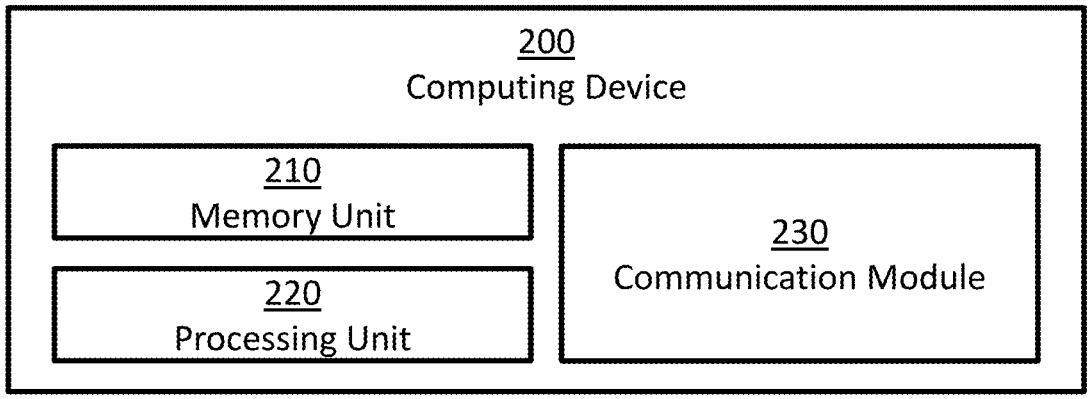
FIGS. 2A and 2B are block diagrams illustrating some possible implementations of a computing device.

FIG. 2A is a block diagram illustrating a possible implementation of computing device 200. In this example, computing device 200 may comprise: one or more memory units 210, one or more processing units 220, and one or more communication modules 230. In some implementations, computing device 200 may comprise additional components, while some components listed above may be excluded.

Figure 2B:
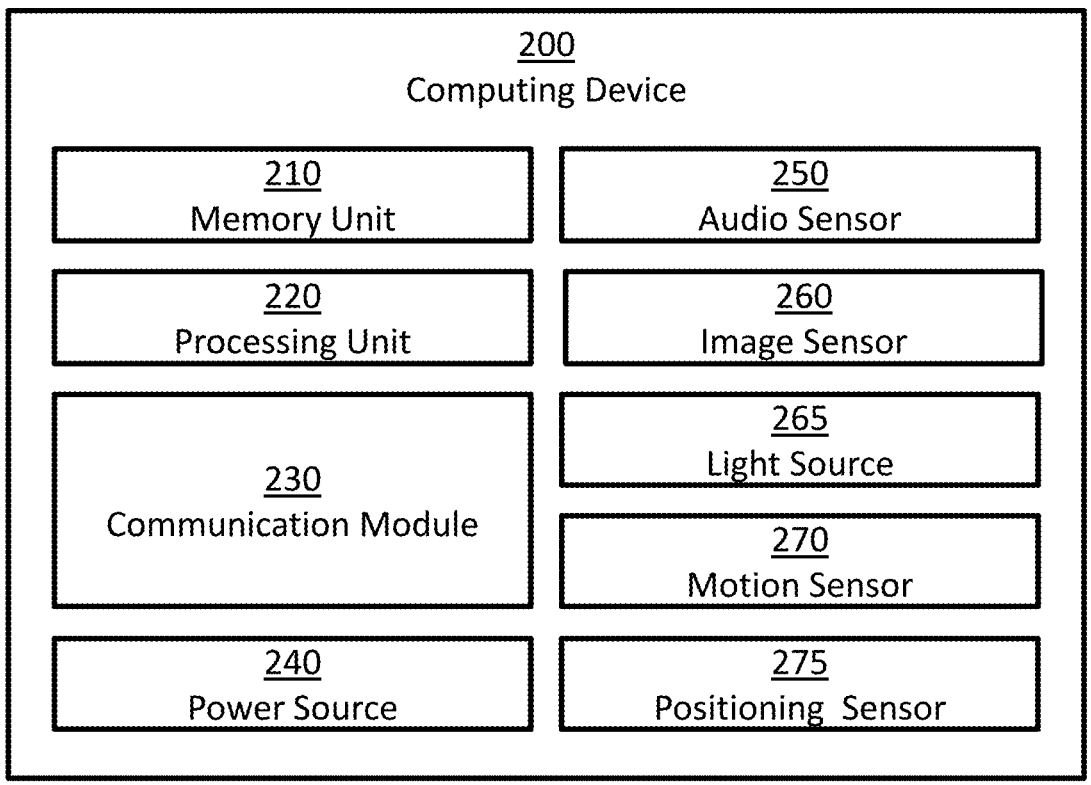

FIG. 2B is a block diagram illustrating a possible implementation of computing device 200. In this example, computing device 200 may comprise: one or more memory units 210, one or more processing units 220, one or more communication modules 230, one or more power sources 240, one or more audio sensors 250, one or more image sensors 260, one or more light sources 265, one or more motion sensors 270, and one or more positioning sensors 275. In some implementations, computing device 200 may comprise additional components, while some components listed above may be excluded. For example, in some implementations computing device 200 may also comprise at least one of the following: one or more barometers; one or more user input devices; one or more output devices; and so forth. In another example, in some implementations at least one of the following may be excluded from computing device 200: memory units 210, communication modules 230, power sources 240, audio sensors 250, image sensors 260, light sources 265, motion sensors 270, and positioning sensors 275.

In some embodiments, one or more power sources 240 may be configured to: power computing device 200, power cloud platform 400, and/or power computational node 500. Possible implementation examples of power sources 240 may include: one or more electric batteries; one or more capacitors; one or more connections to external power sources; one or more power convertors; any combination of the above; and so forth.

In some embodiments, the one or more processing units 220 may be configured to execute software programs. For example, processing units 220 may be configured to execute software programs stored on the memory units 210. In some cases, the executed software programs may store information in memory units 210. In some cases, the executed software programs may retrieve information from the memory units 210. Possible implementation examples of the processing units 220 may include: one or more single core processors, one or more multicore processors; one or more controllers; one or more application processors; one or more system on a chip processors; one or more central processing units; one or more graphical processing units; one or more neural processing units; any combination of the above; and so forth.

In some embodiments, the one or more communication modules 230 may be configured to receive and transmit information. For example, control signals may be transmitted and/or received through communication modules 230. In another example, information received though communication modules 230 may be stored in memory units 210. In an additional example, information retrieved from memory units 210 may be transmitted using communication modules 230. In another example, input data may be transmitted and/or received using communication modules 230. Examples of such input data may include: input data inputted by a user using user input devices; information captured using one or more sensors; and so forth. Examples of such sensors may include: audio sensors 250; image sensors 260; motion sensors 270; positioning sensors 275; chemical sensors; temperature sensors; barometers; and so forth.

In some embodiments, the one or more audio sensors 250 may be configured to capture audio by converting sounds to digital information. Some examples of audio sensors 250 may include: microphones, unidirectional microphones, bidirectional microphones, cardioid microphones, omnidirectional microphones, onboard microphones, wired microphones, wireless microphones, any combination of the above, and so forth. In some examples, the captured audio may be stored in memory units 210. In some additional examples, the captured audio may be transmitted using communication modules 230, for example to other computerized devices, such as cloud platform 400, computational node 500, and so forth. In some examples, processing units 220 may control the above processes. For example, processing units 220 may control at least one of: capturing of the audio; storing the captured audio; transmitting of the captured audio; and so forth. In some cases, the captured audio may be processed by processing units 220. For example, the captured audio may be compressed by processing units 220; possibly followed: by storing the compressed captured audio in memory units 210; by transmitted the compressed captured audio using communication modules 230; and so forth. In another example, the captured audio may be processed using speech recognition algorithms. In another example, the captured audio may be processed using speaker recognition algorithms.

In some embodiments, an image sensor 260 may include a device configured to capture images, a sequence of images, videos, and so forth. This includes sensors that convert optical input into images, where optical input can be visible light (like in a camera), radio waves, microwaves, terahertz waves, ultraviolet light, infrared light, x-rays, gamma rays, and/or any other light spectrum. This also includes both 2D and 3D sensors. Examples of image sensor technologies may include: CCD, CMOS, NMOS, and so forth. 3D sensors may be implemented using different technologies, including: stereo camera, active stereo camera, time of flight camera, structured light camera, radar, range image camera, and so forth. In some examples, the one or more image sensors 260 may be configured to capture visual information by converting light to: images; sequence of images; videos; 3D images; sequence of 3D images; 3D videos; and so forth. In some examples, the captured visual information may be stored in memory units 210. In some additional examples, the captured visual information may be transmitted using communication modules 230, for example to other computerized devices, such as cloud platform 400, computational node 500, and so forth. In some examples, processing units 220 may control the above processes. For example, processing units 220 may control at least one of: capturing of the visual information; storing the captured visual information; transmitting of the captured visual information; and so forth. In some cases, the captured visual information may be processed by processing units 220. For example, the captured visual information may be compressed by processing units 220; possibly followed: by storing the compressed captured visual information in memory units 210; by transmitted the compressed captured visual information using communication modules 230; and so forth. In another example, the captured visual information may be processed in order to: detect objects, detect events, detect action, detect face, detect people, recognize person, and so forth.

In some embodiments, the one or more light sources 265 may be configured to emit light, for example in order to enable better image capturing by image sensors 260. In some examples, the emission of light may be coordinated with the capturing operation of image sensors 260. In some examples, the emission of light may be continuous. In some examples, the emission of light may be performed at selected times. The emitted light may be visible light, infrared light, x-rays, gamma rays, and/or in any other light spectrum. In some examples, image sensors 260 may capture light emitted by light sources 265, for example in order to capture 3D images and/or 3D videos using active stereo method.

In some embodiments, the one or more motion sensors 270 may be configured to perform at least one of the following: detect motion of objects in the environment of computing device 200; measure the velocity of objects in the environment of computing device 200; measure the acceleration of objects in the environment of computing device 200; detect motion of computing device 200; measure the velocity of computing device 200; measure the acceleration of computing device 200; and so forth. In some implementations, the one or more motion sensors 270 may comprise one or more accelerometers configured to detect changes in proper acceleration and/or to measure proper acceleration of computing device 200. In some implementations, the one or more motion sensors 270 may comprise one or more gyroscopes configured to detect changes in the orientation of computing device 200 and/or to measure information related to the orientation of computing device 200. In some implementations, motion sensors 270 may be implemented using image sensors 260, for example by analyzing images captured by image sensors 260 to perform at least one of the following tasks: track objects in the environment of computing device 200; detect moving objects in the environment of computing device 200; measure the velocity of objects in the environment of computing device 200; measure the acceleration of objects in the environment of computing device 200; measure the velocity of computing device 200, for example by calculating the egomotion of image sensors 260; measure the acceleration of computing device 200, for example by calculating the egomotion of image sensors 260; and so forth. In some implementations, motion sensors 270 may be implemented using image sensors 260 and light sources 265, for example by implementing a LIDAR using image sensors 260 and light sources 265. In some implementations, motion sensors 270 may be implemented using one or more RADARs. In some examples, information captured using motion sensors 270: may be stored in memory units 210, may be processed by processing units 220, may be transmitted and/or received using communication modules 230, and so forth.

In some embodiments, the one or more positioning sensors 275 may be configured to obtain positioning information of computing device 200, to detect changes in the position of computing device 200, and/or to measure the position of computing device 200. In some examples, positioning sensors 275 may be implemented using one of the following technologies: Global Positioning System (GPS), GLObal NAvigation Satellite System (GLONASS), Galileo global navigation system, BeiDou navigation system, other Global Navigation Satellite Systems (GNSS), Indian Regional Navigation Satellite System (IRNSS), Local Positioning Systems (LPS), Real-Time Location Systems (RTLS), Indoor Positioning System (IPS), Wi-Fi based positioning systems, cellular triangulation, and so forth. In some examples, information captured using positioning sensors 275 may be stored in memory units 210, may be processed by processing units 220, may be transmitted and/or received using communication modules 230, and so forth.

In some embodiments, the one or more chemical sensors may be configured to perform at least one of the following: measure chemical properties in the environment of computing device 200; measure changes in the chemical properties in the environment of computing device 200; detect the present of chemicals in the environment of computing device 200; measure the concentration of chemicals in the environment of computing device 200. Examples of such chemical properties may include: pH level, toxicity, temperature, and so forth. Examples of such chemicals may include: electrolytes, particular enzymes, particular hormones, particular proteins, smoke, carbon dioxide, carbon monoxide, oxygen, ozone, hydrogen, hydrogen sulfide, and so forth. In some examples, information captured using chemical sensors may be stored in memory units 210, may be processed by processing units 220, may be transmitted and/or received using communication modules 230, and so forth.

In some embodiments, the one or more temperature sensors may be configured to detect changes in the temperature of the environment of computing device 200 and/or to measure the temperature of the environment of computing device 200. In some examples, information captured using temperature sensors may be stored in memory units 210, may be processed by processing units 220, may be transmitted and/or received using communication modules 230, and so forth.

In some embodiments, the one or more barometers may be configured to detect changes in the atmospheric pressure in the environment of computing device 200 and/or to measure the atmospheric pressure in the environment of computing device 200. In some examples, information captured using the barometers may be stored in memory units 210, may be processed by processing units 220, may be transmitted and/or received using communication modules 230, and so forth.

In some embodiments, the one or more user input devices may be configured to allow one or more users to input information. In some examples, user input devices may comprise at least one of the following: a keyboard, a mouse, a touch pad, a touch screen, a joystick, a microphone, an image sensor, and so forth. In some examples, the user input may be in the form of at least one of: text, sounds, speech, hand gestures, body gestures, tactile information, and so forth. In some examples, the user input may be stored in memory units 210, may be processed by processing units 220, may be transmitted and/or received using communication modules 230, and so forth.

In some embodiments, the one or more user output devices may be configured to provide output information to one or more users. In some examples, such output information may comprise of at least one of: notifications, feedbacks, reports, and so forth. In some examples, user output devices may comprise at least one of: one or more audio output devices; one or more textual output devices; one or more visual output devices; one or more tactile output devices; and so forth. In some examples, the one or more audio output devices may be configured to output audio to a user, for example through: a headset, a set of speakers, and so forth. In some examples, the one or more visual output devices may be configured to output visual information to a user, for example through: a display screen, an augmented reality display system, a printer, a LED indicator, and so forth. In some examples, the one or more tactile output devices may be configured to output tactile feedbacks to a user, for example through vibrations, through motions, by applying forces, and so forth. In some examples, the output may be provided: in real time, offline, automatically, upon request, and so forth. In some examples, the output information may be read from memory units 210, may be provided by a software executed by processing units 220, may be transmitted and/or received using communication modules 230, and so forth.

Figure 3:
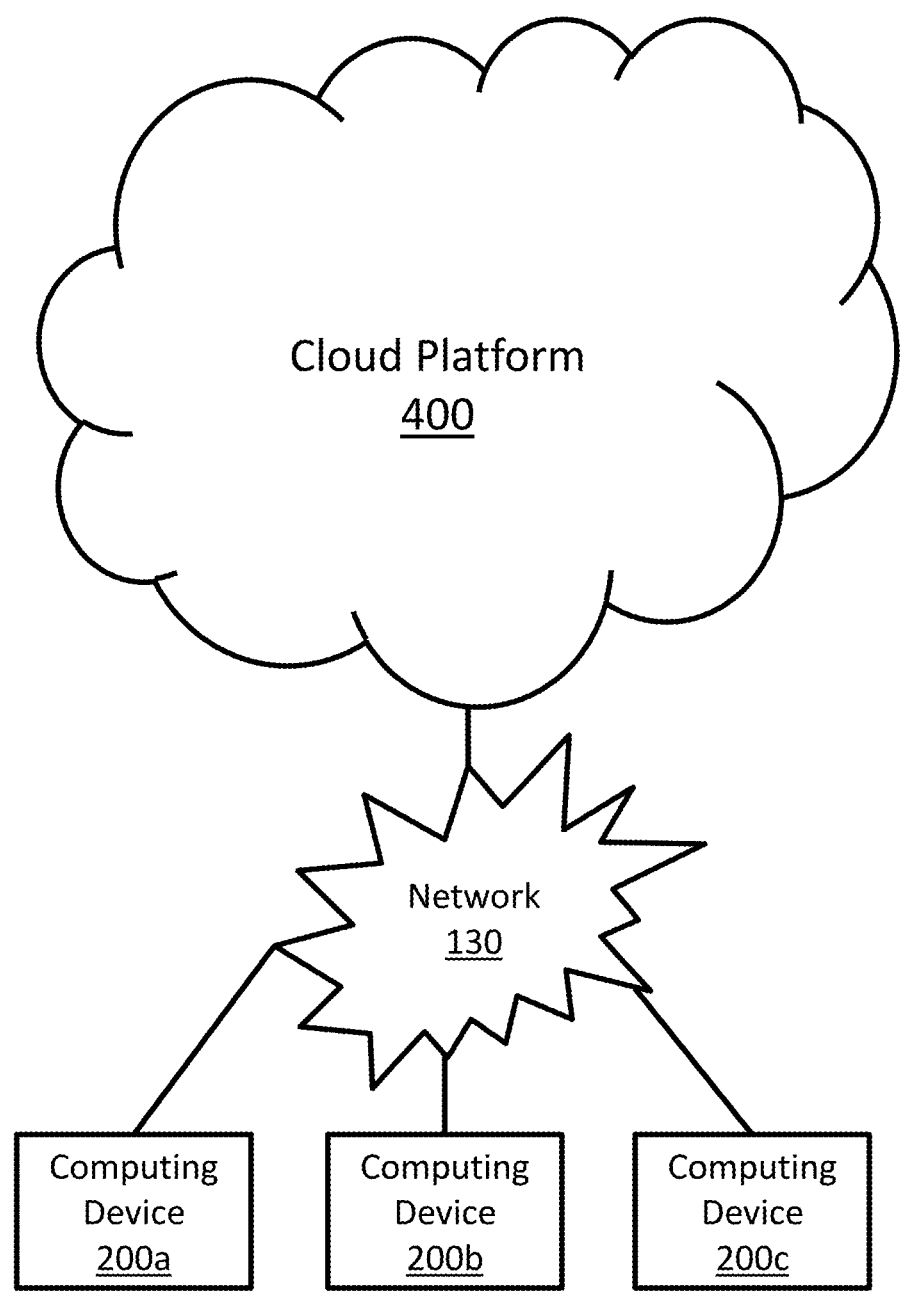
FIG. 3 is a block diagram illustrating a possible implementation of a communicating system.

FIG. 3 is a block diagram illustrating a possible implementation of a communicating system. In this example, computing devices 200a, 200b and 200c may communicate with cloud platform 400 and/or with each other through communication network 130. Possible implementations of computing devices 200a, 200b and 200c may include computing device 200 as described in FIGS. 2A and/or 2B. Some possible implementations of cloud platform 400 are described in FIGS. 4A, 4B and 5.

FIG. 3 illustrates a possible implementation of a communication system. In some embodiments, other communication systems that enable communication among computing devices and/or between a computing device (such as computing device 200) and a cloud platform (such as cloud platform 400) may be used.

Figure 4A:
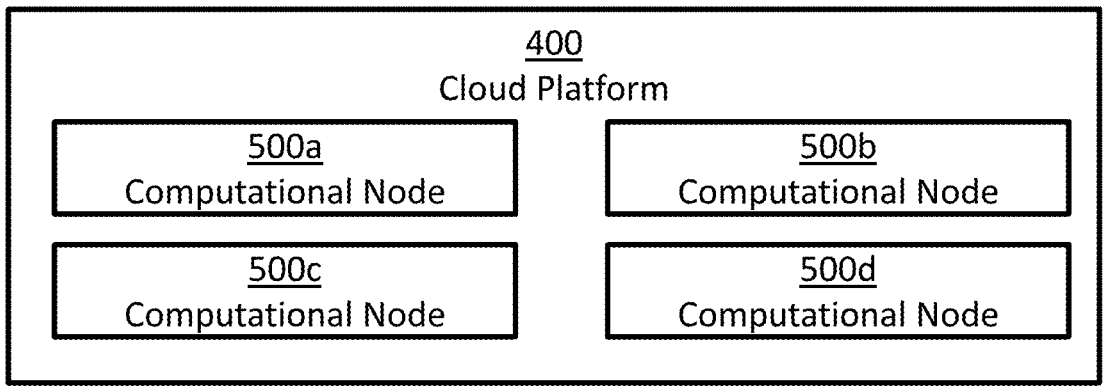
FIGS. 4A and 4B are block diagrams illustrating some possible implementations of a cloud platform.

FIG. 4A is a block diagram illustrating a possible implementation of cloud platform 400. In this example, cloud platform 400 may comprise computational node 500a, computational node 500b, computational node 500c and computational node 500d. In some examples, a possible implementation of computational nodes 500a, 500b, 500c and 500d may comprise computing device 200. In some examples, a possible implementation of computational nodes 500a, 500b, 500c and 500d may comprise computational node 500 as described in FIG. 5.

Figure 4B:
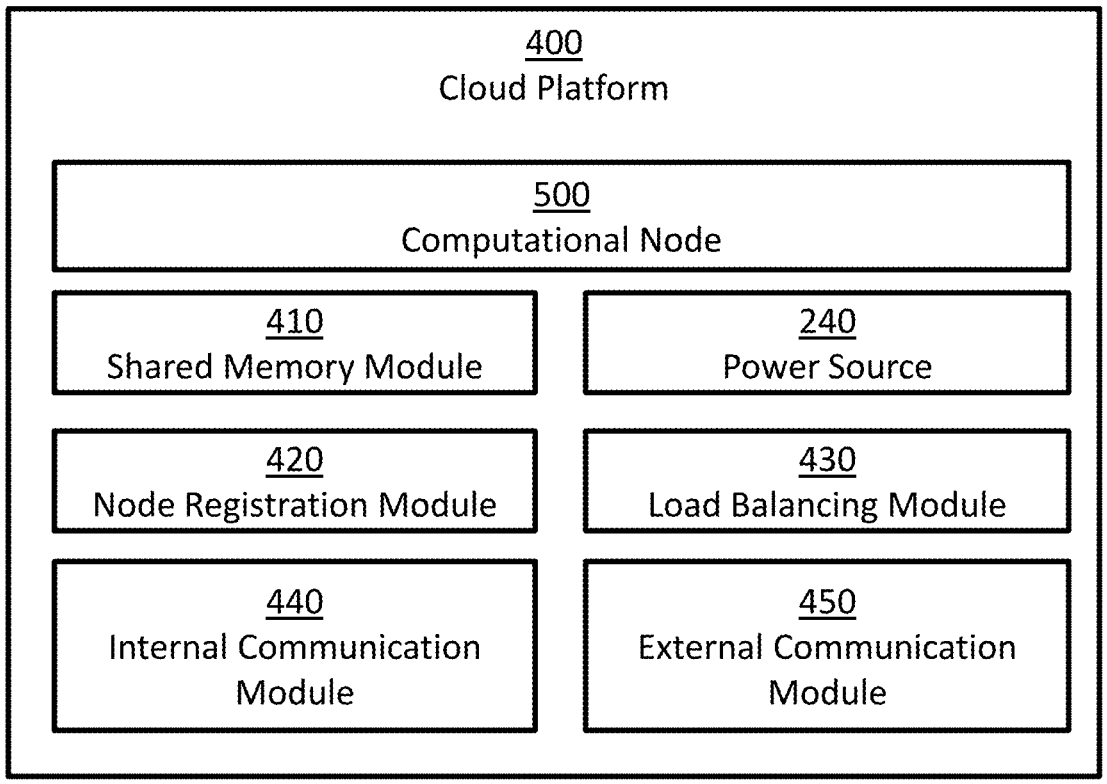

FIG. 4B is a block diagram illustrating a possible implementation of cloud platform 400. In this example, cloud platform 400 may comprise: one or more computational nodes 500, one or more shared memory modules 410, one or more power sources 240, one or more node registration modules 420, one or more load balancing modules 430, one or more internal communication modules 440, and one or more external communication modules 450. In some implementations, cloud platform 400 may comprise additional components, while some components listed above may be excluded. For example, in some implementations cloud platform 400 may also comprise at least one of the following: one or more user input devices; one or more output devices; and so forth. In another example, in some implementations at least one of the following may be excluded from cloud platform 400: shared memory modules 410, power sources 240, node registration modules 420, load balancing modules 430, internal communication modules 440, and external communication modules 450.

Figure 5:
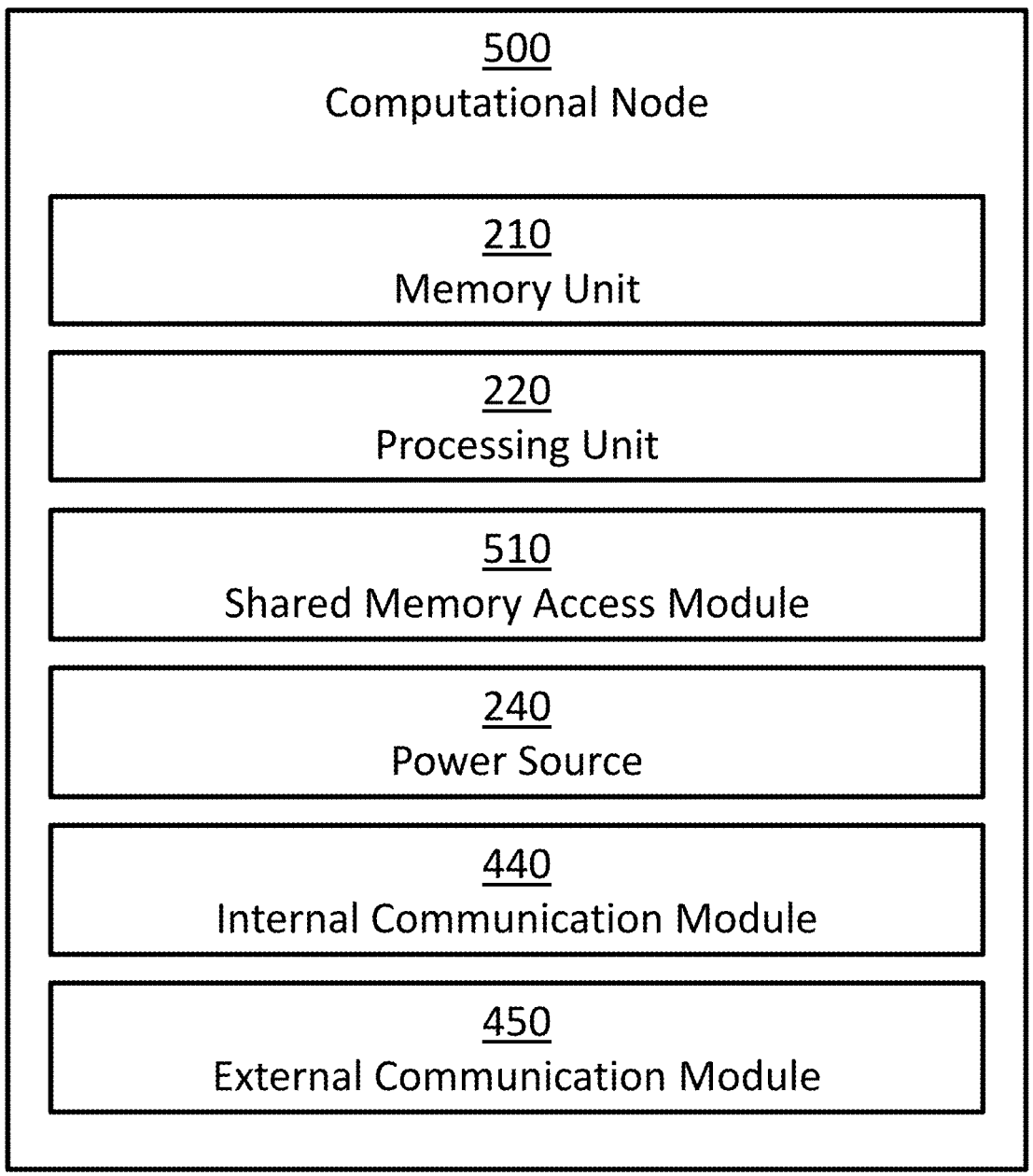
FIG. 5 is a block diagram illustrating a possible implementation of a computational node.

FIG. 5 is a block diagram illustrating a possible implementation of computational node 500. In this example, computational node 500 may comprise: one or more memory units 210, one or more processing units 220, one or more shared memory access modules 510, one or more power sources 240, one or more internal communication modules 440, and one or more external communication modules 450. In some implementations, computational node 500 may comprise additional components, while some components listed above may be excluded. For example, in some implementations computational node 500 may also comprise at least one of the following: one or more user input devices; one or more output devices; and so forth. In another example, in some implementations at least one of the following may be excluded from computational node 500: memory units 210, shared memory access modules 510, power sources 240, internal communication modules 440, and external communication modules 450.

In some embodiments, internal communication modules 440 and external communication modules 450 may be implemented as a combined communication module, such as communication modules 230. In some embodiments, one possible implementation of cloud platform 400 may comprise computing device 200. In some embodiments, one possible implementation of computational node 500 may comprise computing device 200. In some embodiments, one possible implementation of shared memory access modules 510 may comprise using internal communication modules 440 to send information to shared memory modules 410 and/or receive information from shared memory modules 410. In some embodiments, node registration modules 420 and load balancing modules 430 may be implemented as a combined module.

In some embodiments, the one or more shared memory modules 410 may be accessed by more than one computational node. Therefore, shared memory modules 410 may allow information sharing among two or more computational nodes 500. In some embodiments, the one or more shared memory access modules 510 may be configured to enable access of computational nodes 500 and/or the one or more processing units 220 of computational nodes 500 to shared memory modules 410. In some examples, computational nodes 500 and/or the one or more processing units 220 of computational nodes 500, may access shared memory modules 410, for example using shared memory access modules 510, in order to perform at least one of: executing software programs stored on shared memory modules 410, store information in shared memory modules 410, retrieve information from the shared memory modules 410.

In some embodiments, the one or more node registration modules 420 may be configured to track the availability of the computational nodes 500. In some examples, node registration modules 420 may be implemented as: a software program, such as a software program executed by one or more of the computational nodes 500; a hardware solution; a combined software and hardware solution; and so forth. In some implementations, node registration modules 420 may communicate with computational nodes 500, for example using internal communication modules 440. In some examples, computational nodes 500 may notify node registration modules 420 of their status, for example by sending messages: at computational node 500 startup; at computational node 500 shutdown; at constant intervals; at selected times; in response to queries received from node registration modules 420; and so forth. In some examples, node registration modules 420 may query about computational nodes 500 status, for example by sending messages: at node registration module 420 startup; at constant intervals; at selected times; and so forth.

In some embodiments, the one or more load balancing modules 430 may be configured to divide the work load among computational nodes 500. In some examples, load balancing modules 430 may be implemented as: a software program, such as a software program executed by one or more of the computational nodes 500; a hardware solution; a combined software and hardware solution; and so forth. In some implementations, load balancing modules 430 may interact with node registration modules 420 in order to obtain information regarding the availability of the computational nodes 500. In some implementations, load balancing modules 430 may communicate with computational nodes 500, for example using internal communication modules 440. In some examples, computational nodes 500 may notify load balancing modules 430 of their status, for example by sending messages: at computational node 500 startup; at computational node 500 shutdown; at constant intervals; at selected times; in response to queries received from load balancing modules 430; and so forth. In some examples, load balancing modules 430 may query about computational nodes 500 status, for example by sending messages: at load balancing module 430 startup; at constant intervals; at selected times; and so forth.

In some embodiments, the one or more internal communication modules 440 may be configured to receive information from one or more components of cloud platform 400, and/or to transmit information to one or more components of cloud platform 400. For example, control signals and/or synchronization signals may be sent and/or received through internal communication modules 440. In another example, input information for computer programs, output information of computer programs, and/or intermediate information of computer programs, may be sent and/or received through internal communication modules 440. In another example, information received though internal communication modules 440 may be stored in memory units 210, in shared memory units 410, and so forth. In an additional example, information retrieved from memory units 210 and/or shared memory units 410 may be transmitted using internal communication modules 440. In another example, input data may be transmitted and/or received using internal communication modules 440. Examples of such input data may include input data inputted by a user using user input devices.

In some embodiments, the one or more external communication modules 450 may be configured to receive and/or to transmit information. For example, control signals may be sent and/or received through external communication modules 450. In another example, information received though external communication modules 450 may be stored in memory units 210, in shared memory units 410, and so forth. In an additional example, information retrieved from memory units 210 and/or shared memory units 410 may be transmitted using external communication modules 450. In another example, input data may be transmitted and/or received using external communication modules 450. Examples of such input data may include: input data inputted by a user using user input devices; information captured from the environment of computing device 200 using one or more sensors; and so forth. Examples of such sensors may include: audio sensors 250; image sensors 260; motion sensors 270; positioning sensors 275; chemical sensors; temperature sensors; barometers; and so forth.

Figure 6:
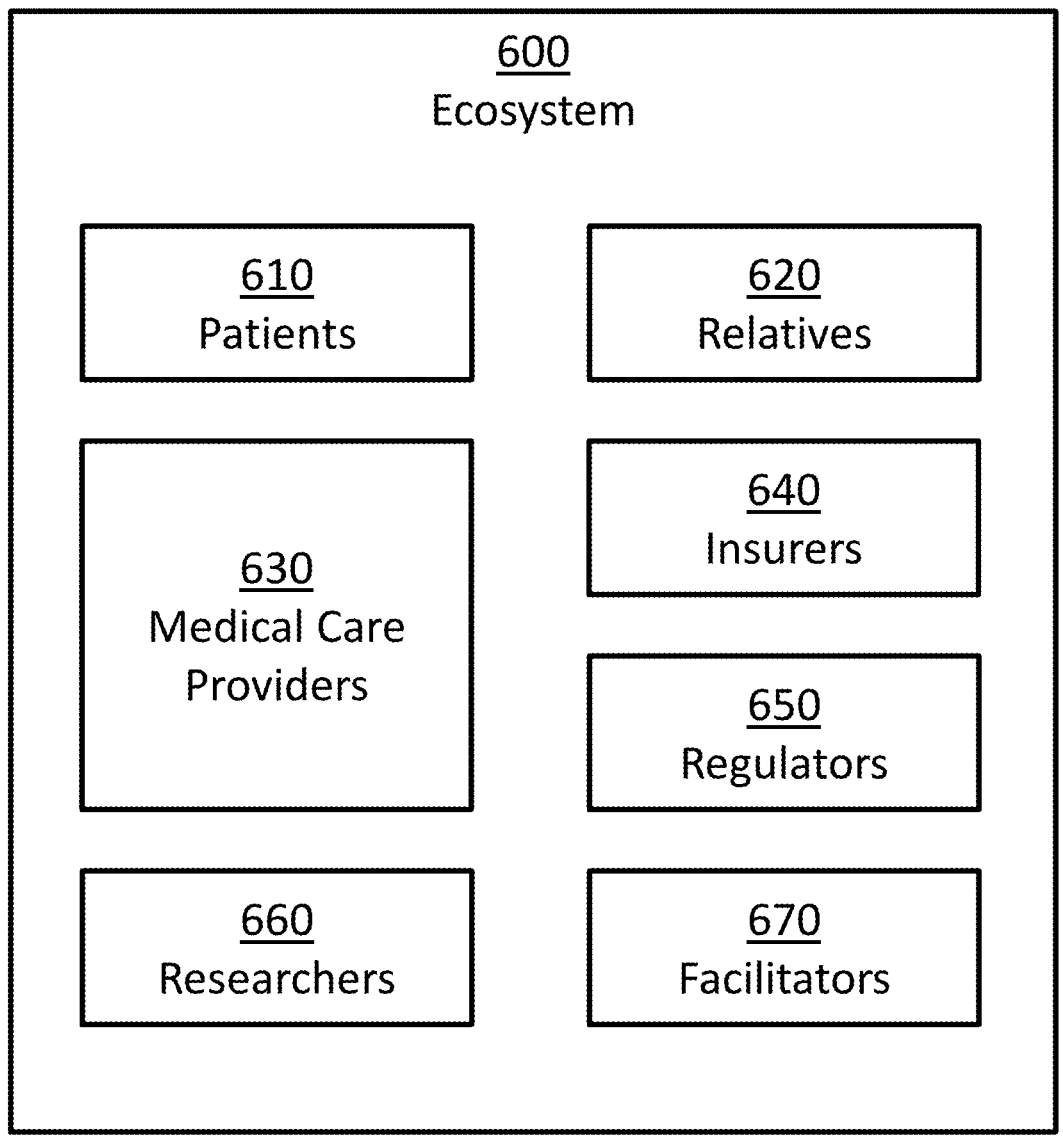
FIG. 6 is a block diagrams illustrating a possible ecosystem.

FIG. 6 is a block diagrams illustrating a possible ecosystem 600. In this example, the ecosystem may comprise one or more patients 610, one or more relatives 620, one or more medical care providers 630, one or more insurers 640, one or more regulators 650, one or more researchers 660, and one or more facilitators 670. In some embodiments, other ecosystems may exist. In some examples, ecosystem 600 may comprise one or more additional entities, while some of the entities listed above may be excluded from ecosystem 600. For example, patients 610 and/or relatives 620 and/or medical care providers 630 and/or insurers 640 and/or regulators 650 and/or researchers 660 and/or facilitators 670 may be excluded from ecosystem 600. For example, ecosystem 600 may further include financial institutes (such as banks, credit companies, etc.), legal firms, non-medical service providers, research institutes, and so forth.

In some embodiments, entities of ecosystem 600 (such as patients 610, relatives 620, medical care providers 630, insurers 640, regulators 650, researcher 660, facilitators 670, etc.) may use computerized devices (such as computing device 200, computational node 500, cloud platform 400, etc.) to perform part and/or all of their functions and/or duties. For example, the entities may use computerized devices to store and/or access and/or process data (some examples of such data may include medical records 710, scheduling records 720, financial records 730, insurance records 740, research records 750, indexes 760, identifiers 770, and/or permissions 780 described below), to communicate (for example over communication network 130), and so forth.

In some embodiments, patients 610 may comprise one or more individuals that received and/or are about to receive medical care.

In some embodiments, relatives 620 may comprise one or more individuals that have some bearing on the medical care of at least one patient 610. For example, relatives 620 may comprise one or more of a family member of patient 610, a friend of patient 610, a legal guardian of patient 610, a next of kin of patient 610, a non-medical care giver of patient 610, and so forth.

In some embodiments, medical care providers 630 may comprise one or more individual and/or one or more institutes that provides (in the past and/or present and/or future) medical care to patients 610. For example, medical care providers 630 may comprise one or more medical care professionals (such as medical doctors, nurses, therapists, stuff of medical care institutes, etc.), one or more medical care institutes (such as hospitals, clinics, labs, etc.), and so forth.

In some embodiments, insurers 640 may comprise one or more individuals and/or one or more institutes that cover medical expenses (such as medical expenses of at least some of patients 610 and/or medical care providers 630) and/or insures medical care providers 630 for malpractice costs. In some examples, insurers may include insurance firms and/or government agencies.

In some embodiments, regulators 650 may comprise official entities appointed to track and/or regulate the medical care provided to patents 610 and/or the medical care provided by medical care providers 630 and/or the medical care covered by insurers 640. For example, regulators 650 may comprise government agencies (such as the FDA, NIH, EMA, CFDA, PMDA, etc.), professional associations (such as the WMA, AMA, EMA, CMA, JMA, etc.), court appointed oversight, and so forth.

In some embodiments, researcher 660 may comprise research personals, research facilities, research institutes, research teams (such as teams 140A, 140B and 140C), and so forth. For example, researchers 660 may comprise a university, a drug development company, a research professor, and so forth.

In some embodiments, facilitators 670 may comprise individuals and/or entities that facilitate the communication among entities of ecosystem 600.

Figure 7:
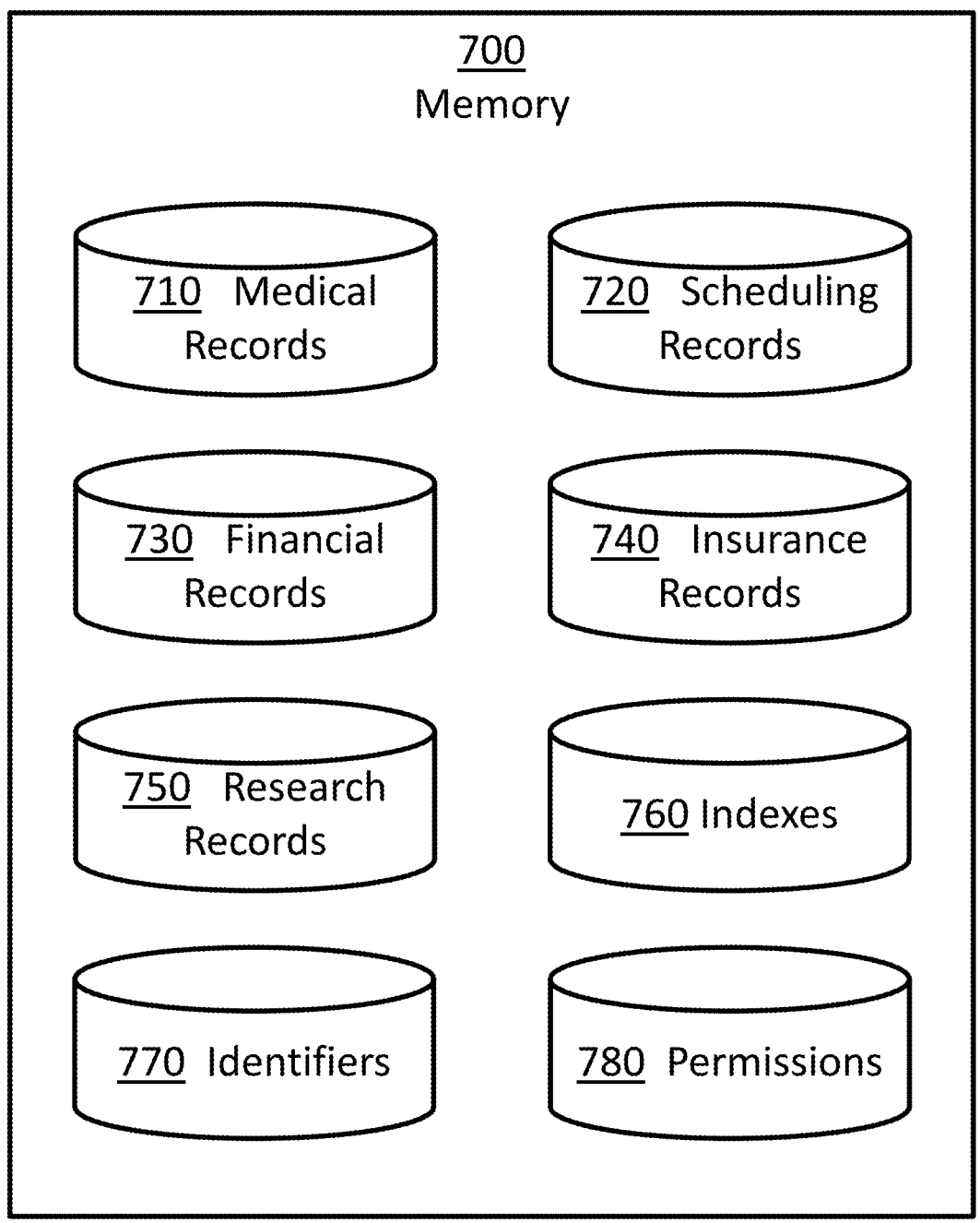
FIG. 7 illustrates an exemplary embodiment of a memory storing a plurality of modules.

FIG. 7 illustrates an exemplary embodiment of memory 700 storing a plurality of modules. In some examples, memory 700 may be separate from and/or integrated with memory units 210, separate from and/or integrated with memory units 410, and so forth. In some examples, memory 700 may be included in a single device, for example in computing device 200, in cloud platform 400, in computational node 500, and so forth. In some examples, memory 700 may be distributed across several devices. Memory 700 may store more or fewer modules than those shown in FIG. 7. In this example, memory 700 may comprise: medical records 710, scheduling records 720, financial records 730, insurance records 740, research records 750, indexes 760, identifiers 770, and permissions 780.

In some embodiments, at least part of medical records 710 scheduling records 720, financial records 730, insurance records 740, research records 750, indexes 760, identifiers 770, and/or permissions 780 may be stored in a public database, in a public ledger, in a blockchain, in a computerized devices (such as computing device 200, cloud platform 400, computational node 500, etc.), in a storage devices (such as remote storage, network attached storage, etc.), and so forth. In some examples, medical records 710, scheduling records 720, financial records 730, insurance records 740, research records 750, indexes 760, identifiers 770, and/or permissions 780 may be stored in single database and/or blockchain and/or site and/or device, while in other examples medical records 710 may be distributed among a number of databases and/or blockchains and/or sites and/or devices. In some examples, medical records of a single entity (such as patient 610, relative 620, medical care provider 630, insurer 640, regulator 650, researcher 660, facilitator 670, etc.) may be stored in single database and/or blockchain and/or site and/or device, while in other examples the medical records of the entity may be distributed among a number of databases and/or blockchains and/or sites and/or devices.

In some embodiments, medical records 710 may comprise medical records of one or more patients 610, medical records created and/or used by one or more medical care providers 630, medical records associated with one or more patients and/or medical care providers insured by one or more insurers 640, medical records surveyed by one or more regulators 650, medical records studied by one or more researchers 660, and so forth. In some examples, medical records 710 may comprise medical information, such as information regarding medical conditions, medical care, medical treatment, EHR, genome data, and so forth.

In some embodiments, scheduling records 720 may comprise scheduling related information associated with patients 610 and/or relatives 620 and/or medical care providers 630 and/or insurers 640 and/or regulators 650 and/or researchers 660 and/or facilitators 670. The scheduling related information may relate to past and/or present and/or future events. For example, scheduling records 720 may comprise time and date information for an appointment, for a lab test, for a medical exam, for a medical checkup, for a reminder related to medical care, and so forth.

In some embodiments, financial records 730 may comprise financial information associated with patients 610 and/or relatives 620 and/or medical care providers 630 and/or insurers 640 and/or regulators 650 and/or researchers 660 and/or facilitators 670. The financial information may relate to past, present, and/or future budget, costs, bills, coverage obligations, and/or payments associated with medical care.

In some embodiments, insurance records 740 may comprise insurance information associated with patients 610 and/or relatives 620 and/or medical care providers 630 and/or insurers 640 and/or regulators 650 and/or researchers 660 and/or facilitators 670. The insurance information may include past, present and/or future coverage information, insurance claims, insurance payments, and so forth, associated with medical care.

In some embodiments, research records 750 may comprise research records associated with patients 610 and/or relatives 620 and/or medical care providers 630 and/or insurers 640 and/or regulators 650 and/or researchers 660 and/or facilitators 670. For example, research records 750 may comprise research records compiled and/or studied by a researcher 660. For example, research records 750 may comprise research records pertaining to one or more medical researches.

In some embodiments, indexes 760 may comprise one or more partial and/or complete indexes. In some examples, an index may link an identifier of a record (such as medical record 710 scheduling record 720, financial record 730, insurance record 740, research record 750, index 760, identifiers 770, permission 780, etc.) to entities (such as patients 610, relatives 620, medical care providers 630, insurers 640, regulators 650, researchers 660, facilitators 670, and so forth). For example, an index may link an identifier of a record to the entity created the record, to entities that accessed and/or edited the record, to entities that has permission to access and/or edit the record, and so forth.

In some examples, an index may link an identifier of an entity (such as patient 610, relative 620, medical care provider 630, insurer 640, regulator 650, researcher 660, facilitator 670, etc.) to records (such as medical records 710 scheduling records 720, financial records 730, insurance records 740, research records 750, indexes 760, identifiers 770, permissions 780, etc.) associated with the entity, to records that the entity has permissions to access and/or edit, to records accessed and/or edited by the entity, and so forth.

In some examples, an index may link an identifier of an entity (such as patient 610, relative 620, medical care provider 630, insurer 640, regulator 650, researcher 660, facilitator 670, etc.) to computerized devices (such as computing device 200, computational node 500, cloud platform 400, etc.) and/or to storage devices (such as remote storage, network attached storage, etc.) and/or to blockchains and/or to databases containing information and/or at least part of the records (such as medical records 710 scheduling records 720, financial records 730, insurance records 740, research records 750, indexes 760, identifiers 770, permissions 780, etc.) associated with the entity.

In some examples, an index may link an identifier of an entity (such as patient 610, relative 620, medical care provider 630, insurer 640, regulator 650, researcher 660, facilitator 670, etc.) to other entities (such as patient 610, relative 620, medical care provider 630, insurer 640, regulator 650, researcher 660, facilitator 670, and so forth). For example, an index may link an identifier of a patient 610 to relatives 620 related to the patient, medical care providers 630 that created and/or hold at least part of the records associated with the patient, to medical care providers 630 that hold permissions to access and/or edit at least parts of the records associated with the patient, to medical care providers 630 that accessed and/or edited at least parts of the records associated with the patient, to one or more insurers 640 associated with the patient, to regulators 650 dealing with medical information related to the patient, to researchers 660 studying medical information related to the patient, and so forth. For example, an index may link an identifier of a relative 620 to a patient 610 related to the relative and/or to entities associated with that patient. For example, an index may link an identifier of a medical care provider 630 to patients 610 and/or relatives of patient 620 that the medical care provider treat and/or has permissions to access and/or edit at least part of their medical records, to other medical care providers 630 that work in conjunction with the medical care provider, to insurer 640 of the medical care provider and/or patients of the medical care provider and/or employees of the medical care provider and/or suppliers of the medical care provider, to regulators 650 supervising the medical care provider, to researchers 660 working with and/or for the medical care provider, and so forth. For example, an index may link an identifier of an insurer 640 to entities insured by the insurer. For example, an index may link an identifier of a regulator 650 to entities supervised by the regulator. For example, an index may link an identifier of a researcher 660 to entities studied by the researcher, to entities working in conjunction with the researcher, and so forth. For example, an index may link an identifier of a facilitator 670 to entities recognized by and/or associated with the facilitator.

In some embodiments, identifiers 770 may comprise identifiers of entities (such as patients 610, relatives 620, medical care providers 630, insurers 640, regulators 650, researchers 660, facilitators 670, etc.) and/or records (such as medical records 710 scheduling records 720, financial records 730, insurance records 740, research records 750, indexes 760, permissions 780, and so forth). In some examples, identifier of an entity and/or record may be unique, while in other examples more than one identifier may identify the same entity and/or record.

In some embodiments, permissions 780 may specify which entities (such as patients 610, relatives 620, medical care providers 630, insurers 640, regulators 650, researchers 660, facilitators 670, etc.) may create and/or edit and/or access which records (such as medical records 710 scheduling records 720, financial records 730, insurance records 740, research records 750, indexes 760, identifiers 770, permissions 780, and so forth). For example, permissions 780 may comprise a group or entities allowed to create and/or edit and/or access selected records, a group or entities prohibited from creating and/or editing and/or accessing selected records, and so forth. For example, the selected records above may be specified as a group of records, as a rule defining a group of records, as the records associated with selected entities, and so forth. In some examples, permissions 780 may further specify which entities are allowed to grant which permission to which other entities regarding which records.

In some embodiments, medical care providers 630 may create and/or edit records of a patient 610 (such as medical records 710 scheduling records 720, financial records 730, insurance records 740, research records 750, indexes 760, identifiers 770, permissions 780, and so forth). These records may be indexed in indexes 760. These records may be accessed and/or edited by the patient, by some relatives 620 of the patient, by other medical care providers 630 treating the patient, by insurers 640 of the patient and/or the medical care provider, and so forth.

In some embodiments, an insurer 640 may access and/or edit and/or create records (such as medical records 710 scheduling records 720, financial records 730, insurance records 740, research records 750, indexes 760, identifiers 770, permissions 780, etc.) of entities (such as patients 610, relatives 620, medical care providers 630, other insurers 640, regulators 650, researchers 660, facilitators 670, etc.) insured by the insurer.

In some embodiments, a regulator 650 may access and/or edit and/or create records (such as medical records 710 scheduling records 720, financial records 730, insurance records 740, research records 750, indexes 760, identifiers 770, permissions 780, etc.) of entities (such as patients 610, relatives 620, medical care providers 630, other insurers 640, regulators 650, researchers 660, facilitators 670, etc.) supervised by the regulator.

In some embodiments, a researcher 660 may access and/or edit and/or create records (such as medical records 710 scheduling records 720, financial records 730, insurance records 740, research records 750, indexes 760, identifiers 770, permissions 780, etc.) of entities (such as patients 610, relatives 620, medical care providers 630, other insurers 640, regulators 650, researchers 660, facilitators 670, etc.) studied by the researcher.

In some embodiments, a facilitator 670 may access and/or edit and/or create records (such as medical records 710 scheduling records 720, financial records 730, insurance records 740, research records 750, indexes 760, identifiers 770, permissions 780, etc.) of entities (such as patients 610, relatives 620, medical care providers 630, other insurers 640, regulators 650, researchers 660, facilitators 670, and so forth). For example, a facilitator 670 may create an identifier 770, may verify an identity 770, and so forth. For example, a facilitator 670 may provide permission to relatives 620 of a patient 610 to access the patient's record after the death of the patient by editing permissions 780. For example, a facilitator 670 may recognize an entity as a licensed medical professional, as a licensed insurer, as a legitimate researcher, as a legal regulator, and so forth.

In some embodiments, access to a record and/or creation of a record and/or edition to a record may be recorded, for example in a log, in indexes 760, in the accessed and/or created and/or edited record, and so forth.

In some embodiments, a method, such as methods 800, 820, 830, 840, 860, 880, 900, 920, 930, 940, 950 and 960 etc., may comprise of one or more steps. In some examples, a method, as well as all individual steps therein, may be performed by various aspects of computing device 200, cloud platform 400, computational node 500, and so forth. For example, the method may be performed by processing units 220 executing software instructions stored within memory units 210 and/or within shared memory modules 410. In some examples, a method, as well as all individual steps therein, may be performed by a dedicated hardware. In some examples, computer readable medium (such as a non-transitory computer readable medium) may store data and/or computer implementable instructions for carrying out a method. Some examples of possible execution manners of a method may include continuous execution (for example, returning to the beginning of the method once the method normal execution ends), periodically execution, executing the method at selected times, execution upon the detection of a trigger (some examples of such trigger may include a trigger from a user, a trigger from another method, a trigger from an external device, etc.), and so forth.

In some embodiments, machine learning algorithms (also referred to as machine learning models in the present disclosure) may be trained using training examples, for example in the cases described below. Some examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear algorithms, non-linear algorithms, ensemble algorithms, and so forth. For example, a trained machine learning algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by an process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters.

In some embodiments, trained machine learning algorithms (also referred to as trained machine learning models in the present disclosure) may be used to analyze inputs and generate outputs, for example in the cases described below. In some examples, a trained machine learning algorithm may be used as an inference model that when provided with an input generates an inferred output. For example, a trained machine learning algorithm may include a classification algorithm, the input may include a sample, and the inferred output may include a classification of the sample (such as an inferred label, an inferred tag, and so forth). In another example, a trained machine learning algorithm may include a regression model, the input may include a sample, and the inferred output may include an inferred value for the sample. In yet another example, a trained machine learning algorithm may include a clustering model, the input may include a sample, and the inferred output may include an assignment of the sample to at least one cluster. In an additional example, a trained machine learning algorithm may include a classification algorithm, the input may include an image, and the inferred output may include a classification of an item depicted in the image. In yet another example, a trained machine learning algorithm may include a regression model, the input may include an image, and the inferred output may include an inferred value for an item depicted in the image (such as an estimated property of the item, such as size, volume, age of a person depicted in the image, cost of a product depicted in the image, and so forth). In an additional example, a trained machine learning algorithm may include an image segmentation model, the input may include an image, and the inferred output may include a segmentation of the image. In yet another example, a trained machine learning algorithm may include an object detector, the input may include an image, and the inferred output may include one or more detected objects in the image and/or one or more locations of objects within the image. In some examples, the trained machine learning algorithm may include one or more formulas and/or one or more functions and/or one or more rules and/or one or more procedures, the input may be used as input to the formulas and/or functions and/or rules and/or procedures, and the inferred output may be based on the outputs of the formulas and/or functions and/or rules and/or procedures (for example, selecting one of the outputs of the formulas and/or functions and/or rules and/or procedures, using a statistical measure of the outputs of the formulas and/or functions and/or rules and/or procedures, and so forth).

In some embodiments, artificial neural networks may be configured to analyze inputs and generate corresponding outputs. Some examples of such artificial neural networks may comprise shallow artificial neural networks, deep artificial neural networks, feedback artificial neural networks, feed forward artificial neural networks, autoencoder artificial neural networks, probabilistic artificial neural networks, time delay artificial neural networks, convolutional artificial neural networks, recurrent artificial neural networks, long short term memory artificial neural networks, and so forth. In some examples, an artificial neural network may be configured manually. For example, a structure of the artificial neural network may be selected manually, a type of an artificial neuron of the artificial neural network may be selected manually, a parameter of the artificial neural network (such as a parameter of an artificial neuron of the artificial neural network) may be selected manually, and so forth. In some examples, an artificial neural network may be configured using a machine learning algorithm. For example, a user may select hyper-parameters for the an artificial neural network and/or the machine learning algorithm, and the machine learning algorithm may use the hyper-parameters and training examples to determine the parameters of the artificial neural network, for example using back propagation, using gradient descent, using stochastic gradient descent, using mini-batch gradient descent, and so forth. In some examples, an artificial neural network may be created from two or more other artificial neural networks by combining the two or more other artificial neural networks into a single artificial neural network.

Figure 8A:
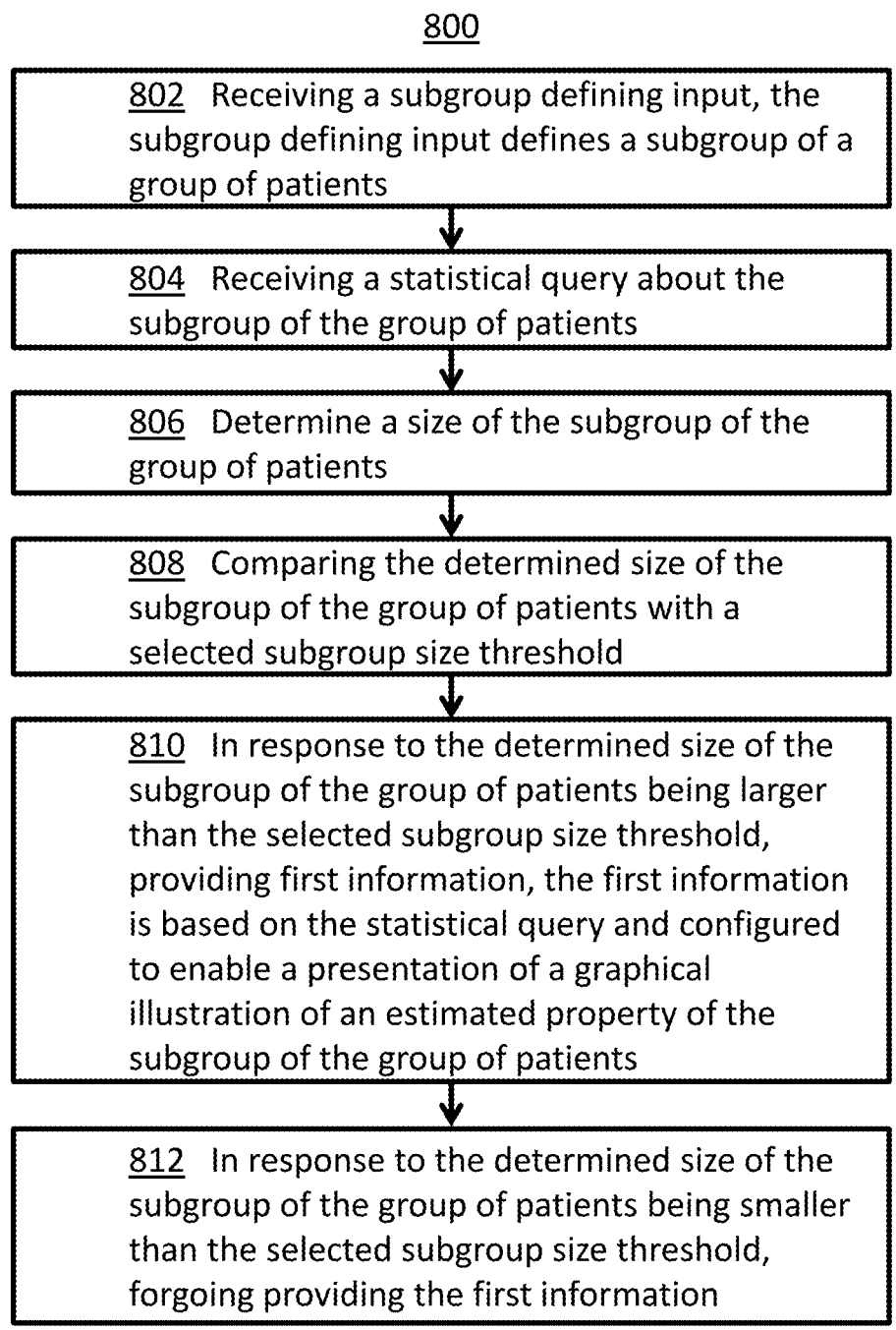
FIG. 8A illustrates an example of a method for enabling graphical illustration based on private medical information.

FIG. 8A illustrates an example of a method 800 for enabling graphical illustration based on private medical information. In this example, method 800 may comprise: receiving a subgroup defining input (Step 802), the subgroup defining input may define a subgroup of a group of patients; receiving a statistical query about the subgroup of the group of patients (Step 804); determine a size of the subgroup of the group of patients (Step 806); comparing the determined size of the subgroup of the group of patients with a selected subgroup size threshold (Step 808); in response to the determined size of the subgroup of the group of patients being larger than the selected subgroup size threshold, providing first information (Step 810), the first information may be based on the statistical query and configured to enable a presentation of a graphical illustration of an estimated property of the subgroup of the group of patients; and in response to the determined size of the subgroup of the group of patients being smaller than the selected subgroup size threshold, forgoing providing the first information (Step 812). In some implementations, method 800 may comprise one or more additional steps, while some of the steps listed above may be modified or excluded. For example, in some cases Step 802 and/or Step 804 and/or Step 806 and/or Step 808 and/or Step 810 and/or Step 812 may be excluded from method 800. In some implementations, one or more steps illustrated in FIG. 8A may be executed in a different order and/or one or more groups of steps may be executed simultaneously and/or a plurality of steps may be combined into single step and/or a single step may be broken down to a plurality of steps. In some examples, after completion of Step 810 and/or Step 812, method 800 may continue to execute method 840 and/or method 860. In some examples, after completion of Step 810, method 800 may continue to execute method 880. In some examples, after completion of Step 812, method 800 may continue to execute method 830.

In some embodiments, Step 802 may comprise receiving a subgroup defining input, where the subgroup defining input may define a subgroup of a group of patients. In some examples, the subgroup defining input may be based on a first input from a user, such as user 146. For example, Step 802 may read at least part of the subgroup defining input from memory (such as memory units 210, shared memory modules 410, and so forth). In another example, Step 802 may receive at least part of the subgroup defining input from an external device (such as computerized data analysis device 144, an external device associated with the user, such as a workstation, a mobile device of the user, etc.) over a communication network using a communication device (such as communication modules 230, internal communication modules 440, external communication modules 450, etc.), may receive at least part of the subgroup defining input from the user (for example, through a user interface, through a web page, using an input device, through computerized data analysis device 144, etc.), and so forth. In one example, the subgroup defining input received by Step 802 may include a query (for example, in a query language such as Structured Query Language) that selects patients of the group of patients to the subgroup of a group of patients. In another example, the subgroup defining input received by Step 802 may include one or more criterions that dictate which patients of the group of patients are included in the subgroup of a group of patients. Some examples on such criterions may include restrictions on the age of the patients (for example, 'patients between the ages of 30 and 40'), restrictions on the gender of the patients (for example, 'female patients'), restrictions on physical characteristics of the patients (for example, 'patients with Body Mass Index under 20'), restriction on ethnicity of the patients (for example, 'Alaskan native patients'), restrictions on demographics of the patients (for example, 'patients with at least two children', 'patients with twelve or more years of education', 'patients with an annual income of at least $30,000', etc.), restrictions on symptoms experienced by the patients (for example, 'patients suffering from back pain'), restrictions on the medical condition of the patients (for example, 'patients suffering from psychiatric disorders'), restriction on durations of medical conditions of the patients (for example, 'patients suffering from fibromyalgia for over a year'), restrictions on the medical treatment received by the patients (for example, 'patients received neuroleptic medication', 'patients who underwent corrective laser eye surgery', etc.), restrictions on adverse effects reported by the patients, restrictions on the medical examinations performed on the patients (for example, 'patients who underwent colonoscopy in the last year'), restrictions on a medical outcome associated with the patients (for example, 'patients with at least one hospital readmission'), restrictions on caregivers of the patients (for example, 'patients treated in a community clinic'), and so forth.

In some embodiments, Step 804 may comprise receiving a statistical query about a subgroup of the group of patients, for example receiving a statistical query about the subgroup of the group of patients defined by the subgroup defining input of Step 802. In some examples, the statistical query may be based on an input from a user (for example, based on a second input from the user of Step 802, based on an input from user 146, based on an input from user 147, and so forth). For example, Step 804 may read at least part of the statistical query about the subgroup of the group of patients from memory (such as memory units 210, shared memory modules 410, and so forth). In another example, Step 804 may receive at least part of the statistical query about the subgroup of the group of patients from an external device (such as computerized data analysis device 144, an external device associated with the user, such as a workstation, a mobile device of the user, etc.) over a communication network using a communication device (such as communication modules 230, internal communication modules 440, external communication modules 450, etc.), may receive at least part of the statistical query about the subgroup of the group of patients from the user (for example, through a user interface, through a web page, using an input device, through computerized data analysis device 144, etc.), and so forth. In one example, the statistical query about the subgroup of the group of patients received by Step 804 may include a query in a query language (such as Structured Query Language) that expresses a statistical query about the subgroup of the group of patients. In another example, the statistical query about the subgroup of the group of patients received by Step 804 may include one or more mathematical formulas for calculating a statistical measure of the subgroup of the group of patients.

In some embodiments, Step 806 may comprise determining a size of a subgroup of a group of patients, for example determining a size of the subgroup of the group of patients defined by the subgroup defining input of Step 802, or determining a size of the updated subgroup of the group of patients of method 840 (described below). For example, Step 806 may determine an exact size of the subgroup of the group of patients, Step 806 may determine an estimated size of the subgroup of the group of patients, and so forth. In one example, Step 806 may count the patients in the subgroup of the group of patients, for example by determining for each patient in the group of patients whether that patient is in the subgroup of the group of patients using the subgroup defining input of Step 802, and the size of the subgroup of the group of patients determined by Step 806 may be the determined number of patients in the subgroup of the group of patients. In another example, Step 806 may estimate the size of the subgroup of the group of patients, for example by determining for each patient in a selected sample of the group of patients whether that patient is in the subgroup of the group of patients using the subgroup defining input of Step 802 to estimate the ratio of patients in the subgroup of the group of patients from the entire group of patients, and using the estimated ratio and a known size of the group of patients to estimate the size of the subgroup of the group of patients. In some examples, a weight may be associated with each patient in the group of patients, and Step 806 may determine a total weight (exact total weight and/or estimated total weight) of the patients in the subgroup of the group of patients, and the size of the subgroup of the group of patients determined by Step 806 may be the determined total weight.

In some embodiments, Step 808 may comprise comparing a size of a subgroup of the group of patients (for example, the size determined by Step 806 of the subgroup of the group of patients defined by the subgroup defining input of Step 802) with a selected subgroup size threshold. For example, Step 808 may read the subgroup size threshold from memory (such as memory units 210, shared memory modules 410, and so forth). In another example, Step 808 may receive the subgroup size threshold from an external device over a communication network using a communication device (such as communication modules 230, internal communication modules 440, external communication modules 450, and so forth). In yet another example, Step 808 may receive the subgroup size threshold from a user (for example, through a user interface, through a web page, using an input device, and so forth). In an additional example, Step 808 may receive the subgroup size threshold as a configuration parameter, for example from a configuration file. In some examples, Step 808 may randomly select the subgroup size threshold from a distribution of thresholds. Some examples of such distribution of thresholds may include discrete distribution, continuous distribution, uniform distribution, binomial distribution, normal distribution, Bernoulli distribution, Poisson distribution, exponential distribution, Polya-Eggenberger distribution, zeta distribution, and so forth. In some examples, Step 808 may select the subgroup size threshold based on whether particular patients are included in the subgroup of the group of patients. For example, in response to the subgroup of the group of patients including a first patient, Step 808 may select a first value for the subgroup size threshold, and in response to the subgroup of the group of patients not including the first patient, Step 808 may select a second value for the subgroup size threshold (the second value differs from the first value). In another example, in response to the subgroup of the group of patients including at least a selected number of patients of a first type, Step 808 may select a first value for the subgroup size threshold, and in response to the subgroup of the group of patients not including at least the selected number of patients of the first type, Step 808 may select a second value for the subgroup size threshold (the second value differs from the first value). For example, the selected number of patients may be one, two, between three and five, above five, and so forth. In another example, Step 808 may select the selected number of patients based on at least one of the first type, the determined size of the subgroup of the group of patients, the size of the group of patients, and so forth. In some examples, Step 808 may select the subgroup size threshold based on a type of the property of the subgroup of the group of patients. For example, in response to the property of the subgroup of the group of patients being of a first type, Step 808 may select a first value for the subgroup size threshold, and in response to the property of the subgroup of the group of patients being of a second type, Step 808 may select a second value for the subgroup size threshold (the second value differs from the first value). In some examples, Step 808 may select the subgroup size threshold based on the user of Step 802. For example, in response to a first user, Step 808 may select a first value for the subgroup size threshold, and in response to a second user, Step 808 may select a second value for the subgroup size threshold (the second value differs from the first value). In another example, Step 808 may select the subgroup size threshold based on at least one of an identity of the user, a type of the user, an identity of a group of at least two users that includes the user, past behavior of the user, at least one previous statistical query that is based on an input from the user, information provided in response to at least one previous statistical query that is based on an input from the user, and so forth. In some examples, Step 808 may select the subgroup size threshold based on at least one previous statistical query about the subgroup of the group of patients. For example, in response to the previous statistical queries about the subgroup of the group of patients including a first statistical query, Step 808 may select a first value for the subgroup size threshold, and in response to the previous statistical queries about the subgroup of the group of patients not including the first statistical query, Step 808 may select a second value for the subgroup size threshold (the second value differs from the first value). In another example, Step 808 may select the subgroup size threshold based on information provided in response to at least one previous statistical query about the subgroup of the group of patients. For example, in response to the information provided in response to at least one previous statistical query having a first property, Step 808 may select a first value for the subgroup size threshold, and in response to at least one previous statistical query not having the first property, Step 808 may select a second value for the subgroup size threshold (the second value differs from the first value).

In some embodiments, Step 810 may comprise providing first information, for example in response to the size determined by Step 806 of the subgroup of the group of patients defined by the subgroup defining input of Step 802 being larger than the selected subgroup size threshold of Step 808. In some examples, the first information may be based on a statistical query (for example, on the statistical query received by Step 804). In some examples, the first information may be configured to enable a presentation of a graphical illustration of an estimated property of a subgroup of the group of patients (for example, of an estimated property of the subgroup of the group of patients defined by the subgroup defining input of Step 802), for example in response to the second input from the user of Step 804. For example, Step 810 may store the first information in memory (such as memory 700, memory units 210, memory modules 410, etc.), in storage device (such as local storage, remote storage, network attached storage, etc.), and so forth. In another example, Step 810 may transmit the first information to an external device, for example over a communication network using a communication device (such as communication modules 230, internal communication modules 440, external communication modules 450, and so forth). In some examples, Step 810 may present the first information to a user, for example through a user interface, through a web page, using an output device (such as a display screen, an augmented reality display system, a printer, a LED indicator, etc.), through computerized data analysis device 144, and so forth.

In some embodiments, Step 812 may comprise forgoing and/or withholding providing the first information of Step 810, for example in response to the size determined by Step 806 of the subgroup of the group of patients defined by the subgroup defining input of Step 802 being smaller than the selected subgroup size threshold of Step 808.

In some examples, provided information (such as the first information provided by Step 810 or Step 834, the second information provided by Step 848, Step 868 or Step 888, the first estimated property of the medical data provided by Step 904, the second estimated property of the medical data provided by Step 912 or by Step 934 or by Step 952, and so forth) may be based on a statistical query (such as the statistical query received by Step 804, the second statistical query received by Step 884, the first statistical query received by Step 902, the second statistical query received by Step 906, and so forth). For example, the first information provided by Step 810 or Step 834 may be based on the statistical query received by Step 804, the second information provided by Step 848 or Step 868 may be based on the statistical query received by Step 804, the second information provided by Step 888 may be based on the second statistical query received by Step 884, the first estimated property of the medical data provided by Step 904 may be based on the first statistical query received by Step 902, the second estimated property of the medical data provided by Step 912 or by Step 934 or by Step 952 may be based on the second statistical query received by Step 906, and so forth. In some examples, the provided information may include information generated using the statistical query. For example, the statistical query may include a query in a query language (such as Structured Query Language), and the provided information may include a result of applying the included query to a database and/or a data structure, or include the result combined with some noise (for example, as generated using method 820 or using method 920). In another example, the statistical query may include a mathematical formula, and the provided information may include a statistical measure of the subgroup of the group of patients and/or of the medical data calculated according to the included mathematical formula, or include the calculated statistical measure combined with some noise (for example, as generated using method 820 or using method 920). In yet another example, information in private medical data 112 and/or memory 700 may be analyzed using the statistical query to determine the provided information.

In some examples, provided information (such as the first information provided by Step 810 or Step 834, the second information provided by Step 848, Step 868 or Step 888, etc.) may be configured to enable and/or cause a presentation of a graphical illustration of an estimated property of a subgroup of the group of patients (for example, of an estimated property of the subgroup of the group of patients defined by the subgroup defining input of Step 802, of an estimated property of the subgroup of the group of patients defined by the second subgroup defining input of Step 882, etc.), for example in response to an input from the user (such as the second input from the user of Step 804, the fourth input from the user of Step 884, and so forth). For example, the estimated property of the subgroup of the group of patients may be an actual property of the subgroup of the group of patients. In another example, the estimated property of the subgroup of the group of patients may be an approximation of an actual property of the subgroup of the group of patients. In some examples, the property of the subgroup of the group of patients to be graphically illustrated may be selected based on the statistical query. For example, in response to a first statistical query, a first property of the subgroup of the group of patients may be graphically illustrated, and in response to a second statistical query, a second property of the subgroup of the group of patients may be graphically illustrated (the second property differs from the first property). Some non-limiting examples of such properties of the subgroup of the group of patients may include a distribution of data associated with the patients in the subgroup of the group of patients, distribution of ages of patients in the subgroup of the group of patients, distribution of genders of patients in the subgroup of the group of patients, distribution of physical characteristics of patients in the subgroup of the group of patients, distribution of ethnicity of patients in the subgroup of the group of patients, distribution of demographic properties of patients in the subgroup of the group of patients, distribution of symptoms experienced by patients in the subgroup of the group of patients, distribution of medical conditions of patients in the subgroup of the group of patients, distribution of durations of medical conditions of patients in the subgroup of the group of patients, distribution of medical treatment received by patients in the subgroup of the group of patients, distribution of adverse effects reported by patients in the subgroup of the group of patients, distribution of medical outcome associated with patients in the subgroup of the group of patients, distribution of properties of caregivers of patients in the subgroup of the group of patients, and so forth.

In some examples, the graphical illustration may include an image. For example, the image may be based on the images associated with the patients of the subgroup of the group of patients. In some examples, each patient of the subgroup of the group of patients may be associated with a medical image, and the graphical illustration may include a display of an image based on the images associated with the patients of the subgroup of the group of patients. Some non-limiting examples of such medical images may include x-rays, computed tomography images, ultrasound images, magnetic resonance images, positron-emission tomography images, color images (for example, of a skin feature, of a medical operation, etc.), images of biopsies, and so forth. For example, the displayed image may be an average image of the images associated with the patients of the subgroup of the group of patients. In another example, the displayed image may be a weighted sum of the images associated with the patients of the subgroup of the group of patients. In yet another example, the displayed image may be a function of the images associated with the patients of the subgroup of the group of patients. In an additional example, at least one pixel of the displayed image may be a weighted sum of a group of pixels, and the group of pixels may comprise at least one pixel from each image of the images associated with the patients of the subgroup of the group of patients. In yet another example, at least one pixel of the displayed image may be a function of a group of pixels, the group of pixels may comprise at least one pixel from each image of the images associated with the patients of the subgroup of the group of patients.

In some examples, the graphical illustration may include a visualization of a correlation matrix. In one example, the graphical illustration may include a visualization of a correlation matrix between survival probabilities of patients of the subgroup of the group of patients and treatment choices associated with the patients of the subgroup of the group of patients. In another example, the graphical illustration may include a visualization of a correlation matrix between outcome associated with patients of the subgroup of the group of patients and demographic characteristics of the patients of the subgroup of the group of patients. In some examples, the graphical illustration may include a visualization of a correlation tensor. For example, the graphical illustration may include a visualization of a correlation tensor visualizing relations among data elements associated with patients of the subgroup of the group of patients.

In some examples, the graphical illustration may include a visualization of correlations between data elements associated with patients of the subgroup of the group of patients. For example, the visualization of the correlations between the data elements may include one or more charts. Some non-limiting examples of such charts may include a bar chart, a plot chart, a line chart, an area chart, a scatter plot, a bubble chart, a column chart, a surface chart, a radar chart, a combo chart, and so forth.

In some examples, the graphical illustration may include a visualization of a distribution of patients with respect to a characteristic of the patients. Some non-limiting examples of such charts may include a pie chart, a donut chart, a histogram, and so forth.

FIG. 8B illustrates an example of a method 820 for determining an estimated property of a subgroup of a group of patients. In this example, method 820 may comprise: obtaining a privacy parameter (Step 822); selecting at least one noise value based on the obtained privacy parameter (Step 824); and combining the at least one noise value with an actual property of a subgroup of a group of patients to determine the estimated property of the subgroup of the group of patients (Step 826). In some implementations, method 820 may comprise one or more additional steps, while some of the steps listed above may be modified or excluded. For example, in some cases Step 822 and/or Step 824 and/or Step 826 may be excluded from method 820. In some implementations, one or more steps illustrated in FIG. 8B may be executed in a different order and/or one or more groups of steps may be executed simultaneously and/or a plurality of steps may be combined into single step and/or a single step may be broken down to a plurality of steps.

In some embodiments, Step 822 may comprise obtaining a privacy parameter. For example, the obtained privacy parameter may comprise at least one of a number, a seed to a pseudo-random number generator, a selection of a noise model, a type of noise distribution, a parameter of a noise distribution, an amount of randomness, and so forth. For example, Step 822 may read at least part of the privacy parameter from memory (such as memory units 210, shared memory modules 410, and so forth). In another example, Step 822 may receive at least part of the privacy parameter from an external device (such as computerized data analysis device 144, an external device associated with the user, such as a workstation, a mobile device of the user, etc.) over a communication network using a communication device (such as communication modules 230, internal communication modules 440, external communication modules 450, and so forth). In yet another example, Step 822 may receive at least part of the privacy parameter from a user (for example, through a user interface, through a web page, using an input device, and so forth). In an additional example, Step 822 may receive at least part of the privacy parameter as a configuration parameter, for example from a configuration file. In some examples, Step 822 may randomly select the privacy parameter from a distribution of privacy parameters. Some examples of such distribution of privacy parameters may include discrete distribution, continuous distribution, uniform distribution, binomial distribution, normal distribution, Bernoulli distribution, Poisson distribution, exponential distribution, Polya-Eggenberger distribution, zeta distribution, and so forth. In some examples, Step 822 may select the privacy parameter based on a size of the subgroup of the group of patients, for example based on the size of the subgroup of the group of patients determined by Step 806. For example, in response to a first determined size of the subgroup of the group of patients, Step 822 may select a first value for the privacy parameter, and in response to a second determined size of the subgroup of the group of patients, Step 822 may select a second value for the privacy parameter (the second value differs from the first value). In some examples, Step 822 may select the privacy parameter based on whether particular patients are included in the subgroup of the group of patients. For example, in response to the subgroup of the group of patients including a first patient, Step 822 may select a first value for the privacy parameter, and in response to the subgroup of the group of patients not including the first patient, Step 822 may select a second value for the privacy parameter (the second value differs from the first value). In another example, in response to the subgroup of the group of patients including at least a selected number of patients of a first type, Step 822 may select a first value for the privacy parameter, and in response to the subgroup of the group of patients not including at least the selected number of patients of the first type, Step 822 may select a second value for the privacy parameter (the second value differs from the first value). For example, the selected number of patients may be one, two, between three and five, above five, and so forth. In another example, Step 822 may select the selected number of patients based on at least one of the first type, the determined size of the subgroup of the group of patients, the size of the group of patients, and so forth. In some examples, Step 822 may select the privacy parameter based on a type of the property of the subgroup of the group of patients. For example, in response to a the property of the subgroup of the group of patients being of a first type, Step 822 may select a first value for the privacy parameter, and in response to the property of the subgroup of the group of patients being of a second type, Step 822 may select a second value for the privacy parameter (the second value differs from the first value). In some examples, Step 822 may select the privacy parameter based on the user of Step 802. For example, in response to a first user, Step 822 may select a first value for the privacy parameter, and in response to a second user, Step 822 may select a second value for the privacy parameter (the second value differs from the first value). In another example, Step 822 may select the privacy parameter based on at least one of an identity of the user, a type of the user, an identity of a group of at least two users that includes the user, past behavior of the user, at least one previous statistical query that is based on an input from the user, information provided in response to at least one previous statistical query that is based on an input from the user, and so forth. In some examples, Step 822 may select the privacy parameter based on at least one previous statistical query about the subgroup of the group of patients. For example, in response to the previous statistical queries about the subgroup of the group of patients including a first statistical query, Step 822 may select a first value for the privacy parameter, and in response to the previous statistical queries about the subgroup of the group of patients not including the first statistical query, Step 822 may select a second value for the privacy parameter (the second value differs from the first value). In another example, Step 822 may select the privacy parameter based on information provided in response to at least one previous statistical query about the subgroup of the group of patients. For example, in response to the information provided in response to at least one previous statistical query having a first property, Step 822 may select a first value for the privacy parameter, and in response to at least one previous statistical query not having the first property, Step 822 may select a second value for the privacy parameter (the second value differs from the first value).

In some embodiments, Step 824 may comprise selecting at least one noise value based on the privacy parameter obtained by Step 822. For example, Step 824 may obtain one or more noise values from a pseudo-random number generator initialized based on the privacy parameter obtained by Step 822 (for example, initialized using a seed included in the privacy parameter). In another example, Step 824 may obtain one or more noise values from a noise model selected from a plurality of alternative noise models based on the privacy parameter obtained by Step 822 (for example, according to an indication of a selected noise model included in the privacy parameter). In yet another example, Step 824 may obtain one or more noise values from a noise distribution, and the type and/or at least part of parameters of the noise distribution may be selected based on the privacy parameter obtained by Step 822 (for example, according to an indication of a type of a noise distribution included in the privacy parameter, according to a parameter of the noise distribution included in the privacy parameter, and so forth). In an additional example, Step 824 may obtain one or more noise values from a list of previously generated random values (for example, the selection of the one or more noise values from the list may be based on the privacy parameter obtained by Step 822). In some examples, the amount of noise values selected by Step 824 may be controlled according to the privacy parameter obtained by Step 822 (for example, according to an amount of randomness specified in the privacy parameter obtained by Step 822).

In some embodiments, Step 826 may combine at least one noise value with an actual property of a subgroup of a group of patients to determine an estimated property of the subgroup of the group of patients. For example, Step 826 may combine the at least one noise value selected by Step 824 with an actual property of the subgroup of the group of patients defined by the subgroup defining input of Step 802 to determine the estimated property of the subgroup of the group of patients. For example, the actual property of the subgroup of the group of patients may include a number, and Step 826 may manipulate the number using a noise value (for example, adding the noise value to the number, multiplying the number by the noise value, etc.) to obtained the estimated property of the subgroup of the group of patients. In another example, the actual property of the subgroup of the group of patients may include a list of details, and Step 826 may manipulate the list of details using the at least one noise value (for example, dropping at least part of the items in the list of details based on the at least one noise value, adding items to the list of details based on the at least one noise value, modifying items in the list of details based on the at least one noise value, switching the order of the items in the list of details based on the at least one noise value, etc.) to obtained the estimated property of the subgroup of the group of patients.

FIG. 8C illustrates an example of a method 830 for enabling graphical illustration based on private medical information. In this example, method 830 may comprise: receiving an indication that an update to a status of the user occurred (Step 832), for example after forgoing providing the first information by Step 812; and in response to the update to the status of the user, providing the first information (Step 834). In some implementations, method 830 may comprise one or more additional steps, while some of the steps listed above may be modified or excluded. For example, in some cases Step 832 and/or Step 834 may be excluded from method 830. In some implementations, one or more steps illustrated in FIG. 8C may be executed in a different order and/or one or more groups of steps may be executed simultaneously and/or a plurality of steps may be combined into single step and/or a single step may be broken down to a plurality of steps. In some examples, method 830 and/or Step 832 may be executed after forgoing providing the first information by Step 812 of method 800.

In some embodiments, Step 832 may comprise receiving an indication that an update to a status of the user of Step 802 occurred, for example after forgoing providing the first information by Step 812 of method 800. For example, Step 832 may receive the indication from a permissions system and/or a permissions database (such as permissions 780), from a repository of regulatory statuses of users, from regulators (such as regulators 650), from a repository of user information, from a repository of employment records (for example, employment records of the user, employment records of medical care providers 630, employment records of insurers 640, employment records of regulators 650, employment records of researchers 660, employment records of facilitators 670, employment records of medical organization 110A, employment records of team 140A, etc.), and so forth. In one example, Step 832 may read the indication from memory (such as memory units 210, shared memory modules 410, and so forth). In another example, Step 832 may receive the indication from an external device over a communication network using a communication device (such as communication modules 230, internal communication modules 440, external communication modules 450, and so forth). In yet another example, Step 832 may receive the indication from a user (for example, through a user interface, through a web page, using an input device, and so forth).

In some embodiments, Step 834 may comprise providing the first information in response to the update to the status of the user. For example, in response to a first update to the status of the user, Step 834 may provide the first information, and in response to a second update to the status of the user, Step 834 may forgo providing the first information. Step 834 may provide the first information as described above in relation to Step 810.

In some examples, the new status of the user may include a new permission, Step 832 may receive an indication that an update to the permissions of the user of Step 802 occurred, and Step 834 may provide the first information in response to the new permission of the user. For example, in response to a first new permission of the user, Step 834 may provide the first information, and in response to a second new permission of the user, Step 834 may forgo providing the first information.

In some examples, the new status of the user may include an approval of an Institutional Review Board for the user to use at least some information, Step 832 may receive an indication that an update to the approvals of the Institutional Review Board for the user of Step 802 occurred, and Step 834 may provide the first information in response to the new approval for the user. For example, in response to a first new approval for the user, Step 834 may provide the first information, and in response to a second new approval for the user, Step 834 may forgo providing the first information.

In some examples, the new status of the user may include a new employment status, Step 832 may receive an indication that an update to the employment status of the user of Step 802 occurred, and Step 834 may provide the first information in response to the new employment status of the user. For example, in response to a first new employment status of the user, Step 834 may provide the first information, and in response to a second new employment status of the user, Step 834 may forgo providing the first information.

Figure 8D:
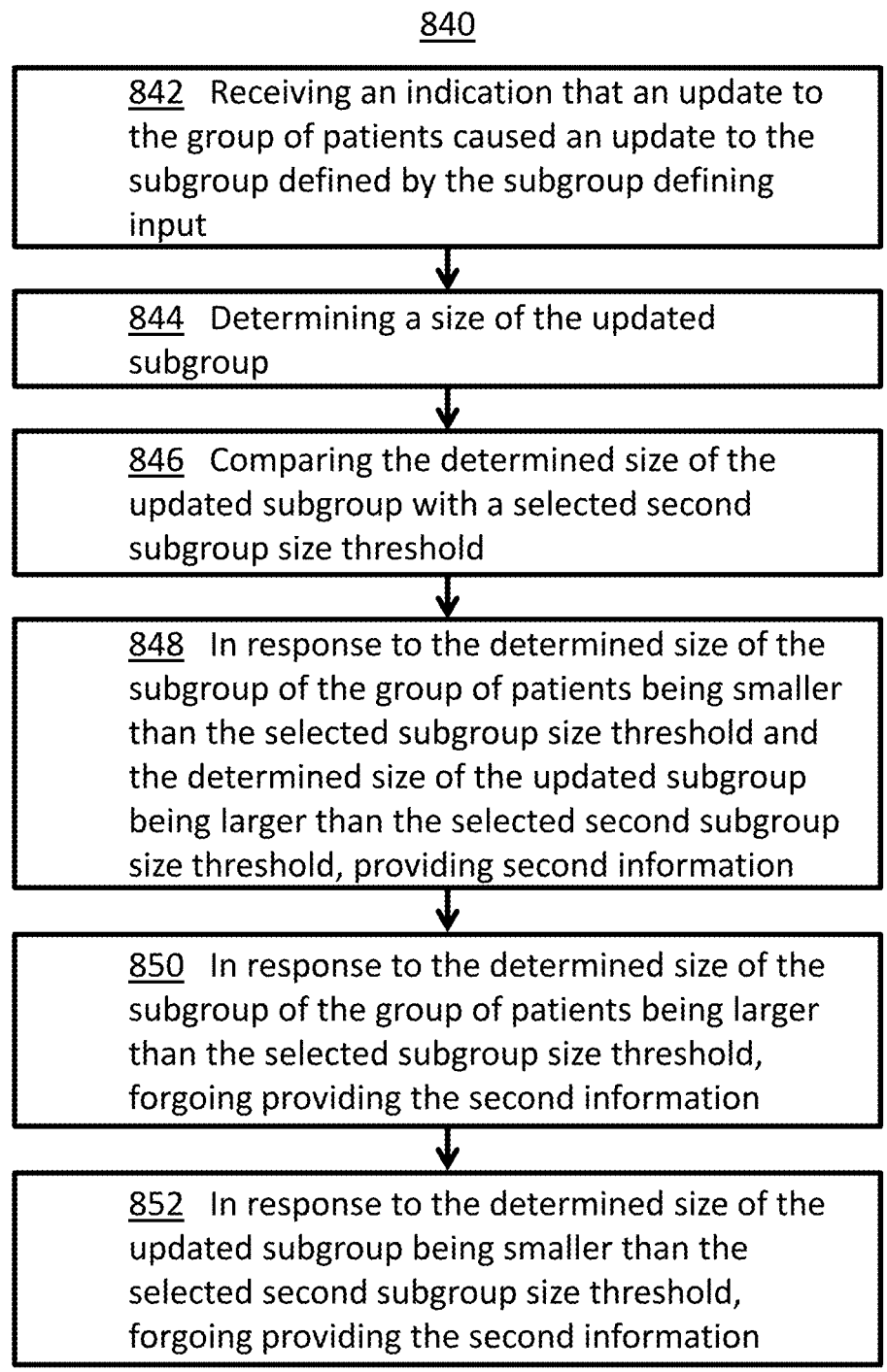
FIG. 8D illustrates an example of a method for enabling graphical illustration based on private medical information.

FIG. 8D illustrates an example of a method 840 for enabling graphical illustration based on private medical information. In this example, method 840 may comprise: receiving an indication that an update to the group of patients caused an update to the subgroup defined by the subgroup defining input (Step 842); determining a size of the updated subgroup (Step 844); comparing the determined size of the updated subgroup with a selected second subgroup size threshold (Step 846); in response to the determined size of the subgroup of the group of patients being smaller than the selected subgroup size threshold and the determined size of the updated subgroup being larger than the selected second subgroup size threshold, providing second information (Step 848), the second information may be based on the statistical query and may be configured to enable a presentation of a graphical illustration of an estimated property of the updated subgroup; in response to the determined size of the subgroup of the group of patients being larger than the selected subgroup size threshold, forgoing providing the second information (Step 850); and in response to the determined size of the updated subgroup being smaller than the selected second subgroup size threshold, forgoing providing the second information (Step 852). In some implementations, method 840 may comprise one or more additional steps, while some of the steps listed above may be modified or excluded. For example, in some cases Step 842 and/or Step 844 and/or Step 846 and/or Step 848 and/or Step 850 and/or Step 852 may be excluded from method 840. In some implementations, one or more steps illustrated in FIG. 8D may be executed in a different order and/or one or more groups of steps may be executed simultaneously and/or a plurality of steps may be combined into single step and/or a single step may be broken down to a plurality of steps. In some examples, method 840 and/or Step 842 may be executed after method 800.

In some embodiments, Step 842 may comprise receiving an indication that an update to the group of patients caused an update to the subgroup defined by the subgroup defining input of Step 802. For example, the group of patients may be patients 610, and Step 842 may receive an indication that an update to patients 610 caused an update to the subgroup defined by the subgroup defining input of Step 802. In another example, Step 842 may read the indication from memory (such as memory units 210, shared memory modules 410, and so forth). In another example, Step 842 may receive the indication from an external device over a communication network using a communication device (such as communication modules 230, internal communication modules 440, external communication modules 450, and so forth). In yet another example, Step 842 may receive the indication from a user (for example, through a user interface, through a web page, using an input device, and so forth). In one example, the updated subgroup of Step 842 may include at least one patient not included in the subgroup of the group of patients defined by the subgroup defining input of Step 802. In another example, the subgroup of the group of patients defined by the subgroup defining input of Step 802 may include at least one patient not included in the updated subgroup of Step 842. In some other examples, the size of the updated subgroup of Step 842 may be larger than the size of the subgroup of the group of patients defined by the subgroup defining input of Step 802, may be identical to the size of the subgroup of the group of patients defined by the subgroup defining input of Step 802, may be smaller than the size of the subgroup of the group of patients defined by the subgroup defining input of Step 802, may be different than the size of the subgroup of the group of patients defined by the subgroup defining input of Step 802, and so forth.

In some embodiments, Step 844 may comprise determining a size of the updated subgroup of Step 842, for example using Step 806 as described above.

In some embodiments, Step 846 may comprise comparing the size of the updated subgroup determined by Step 844 with a selected second subgroup size threshold. For example, the selected second subgroup size threshold may be identical to the selected subgroup size threshold of method 800, may be different from the selected subgroup size threshold of method 800, may be larger than the selected subgroup size threshold of method 800, may be smaller than the selected subgroup size threshold of method 800, and so forth. In some examples, Step 846 may select the second subgroup size threshold based on the selected subgroup size threshold of method 800. For example, in response to a first selected subgroup size threshold of method 800, Step 846 may select a first value for the second subgroup size threshold, and in response to a second selected subgroup size threshold of method 800, Step 846 may select a second value for the second subgroup size threshold (the second value differs from the first value). In some examples, Step 846 may obtain and/or select the second subgroup size threshold in a similar fashion to the selection of the selected subgroup size threshold of method 800 by Step 808 described above.

In some embodiments, Step 848 may comprise providing second information, for example in response to the size of the subgroup of the group of patients of method 800 determined by Step 806 being smaller than the selected subgroup size threshold of Step 808 and the size of the updated subgroup determined by Step 844 being larger than the selected second subgroup size threshold of Step 846. In some examples, the second information may be based on a statistical query (for example, on the statistical query of method 800). In some examples, the second information may be configured to enable a presentation of a graphical illustration of an estimated property of the updated subgroup of Step 842, for example to the user of method 800. For example, Step 848 may provide the second information in a similar fashion to the providence of the first information by Step 810 as described above. In some examples, the second information provided by Step 848 may be identical to the first information of method 800, may be different from the first information of method 800, and so forth.

In some embodiments, Step 850 may comprise forgoing and/or withholding providing the second information of Step 848, for example in response to the size of the subgroup of the group of patients of method 800 determined by Step 806 being larger than the selected subgroup size threshold of Step 808.

In some embodiments, Step 852 may comprise forgoing and/or withholding providing the second information of Step 848, for example in response to the size of the updated subgroup determined by Step 844 being smaller than the selected second subgroup size threshold of Step 846.

Figure 8E:
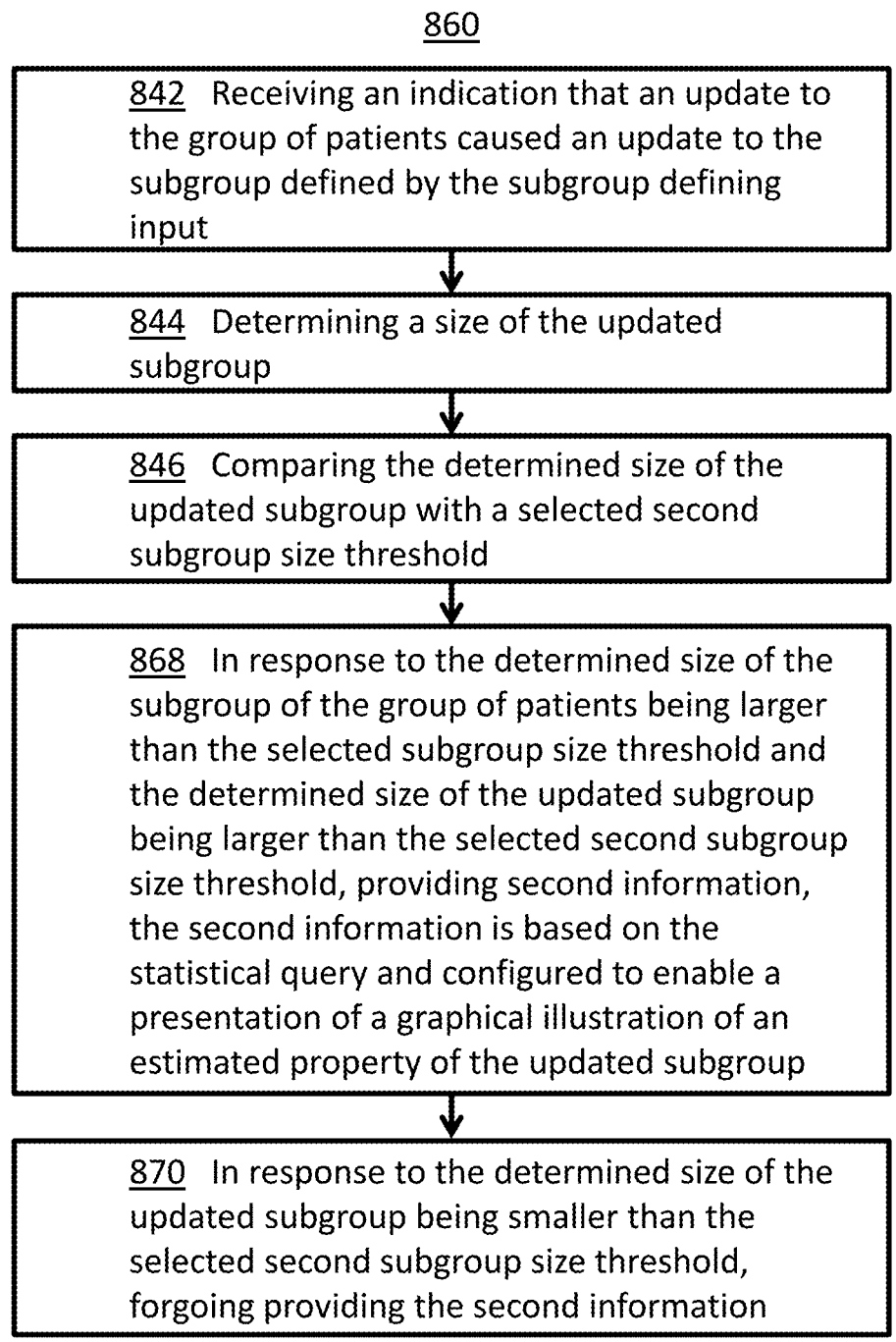
FIG. 8E illustrates an example of a method for enabling graphical illustration based on private medical information.

FIG. 8E illustrates an example of a method 860 for enabling graphical illustration based on private medical information. In this example, method 860 may comprise: receiving an indication that an update to the group of patients caused an update to the subgroup defined by the subgroup defining input (Step 842); determining a size of the updated subgroup (Step 844); comparing the determined size of the updated subgroup with a selected second subgroup size threshold (Step 846); in response to the determined size of the subgroup of the group of patients being larger than the selected subgroup size threshold and the determined size of the updated subgroup being larger than the selected second subgroup size threshold, providing second information (Step 868), the second information may be based on the statistical query and may be configured to enable a presentation of a graphical illustration of an estimated property of the updated subgroup; and in response to the determined size of the updated subgroup being smaller than the selected second subgroup size threshold, forgoing providing the second information (Step 870). In some implementations, method 860 may comprise one or more additional steps, while some of the steps listed above may be modified or excluded. For example, in some cases Step 842 and/or Step 844 and/or Step 846 and/or Step 868 and/or Step 870 may be excluded from method 860. In some implementations, one or more steps illustrated in FIG. 8E may be executed in a different order and/or one or more groups of steps may be executed simultaneously and/or a plurality of steps may be combined into single step and/or a single step may be broken down to a plurality of steps. In some examples, method 860 and/or Step 862 may be executed after providing the first information by Step 810 of method 800.

In some embodiments, Step 868 may comprise providing second information, for example in response to the determined size of the subgroup of the group of patients of method 800 determined by Step 806 being larger than the selected subgroup size threshold of Step 808 and the size of the updated subgroup determined by Step 844 being larger than the selected second subgroup size threshold of Step 846. In some examples, the second information may be based on a statistical query (for example, on the statistical query of method 800). In some examples, the second information may be configured to enable a presentation of a graphical illustration of an estimated property of the updated subgroup of Step 842, for example to the user of method 800. For example, Step 868 may provide the second information in a similar fashion to the providence of the first information by Step 810 as described above. In some examples, the second information provided by Step 868 may be identical to the first information of method 800, may be different from the first information of method 800, and so forth.

In some embodiments, Step 870 may comprise forgoing and/or withholding providing the second information of Step 868, for example in response to the size of the updated subgroup determined by Step 844 being smaller than the selected second subgroup size threshold of Step 846.

In some embodiments, method 860 may further comprise forgoing and/or withholding providing the second information of Step 868, for example in response to the size of the subgroup of the group of patients of method 800 determined by Step 806 being smaller than the selected subgroup size threshold of Step 808.

Figure 8F:
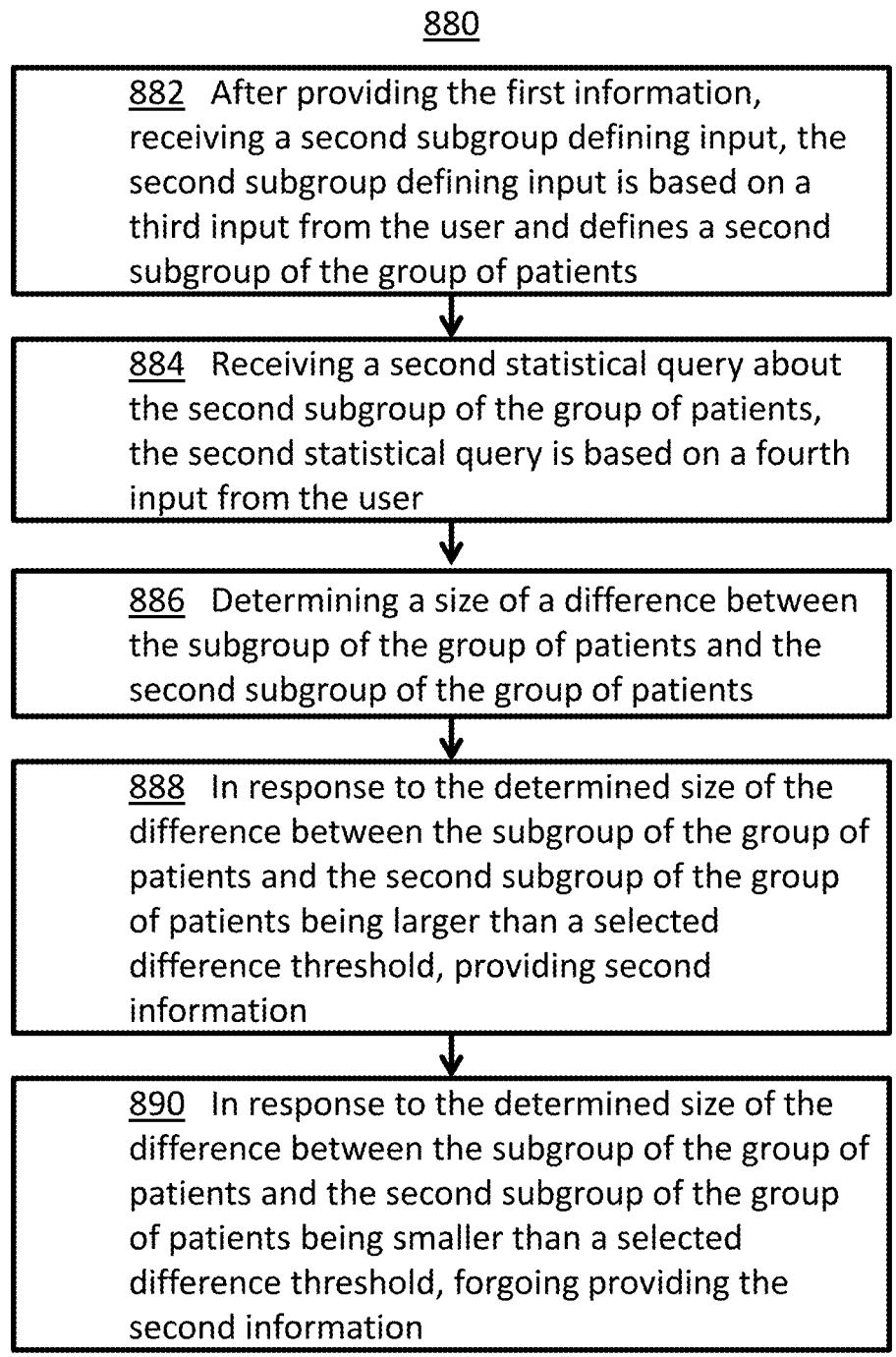
FIG. 8F illustrates an example of a method for enabling graphical illustration based on private medical information.

FIG. 8F illustrates an example of a method 880 for enabling graphical illustration based on private medical information. In this example, method 880 may comprise: receiving a second subgroup defining input (Step 882), for example after providing the first information, the second subgroup defining input may be based on a third input from the user and may define a second subgroup of the group of patients; receiving a second statistical query about the second subgroup of the group of patients (Step 884), the second statistical query may be based on a fourth input from the user; determining a size of a difference between the subgroup of the group of patients and the second subgroup of the group of patients (Step 886); in response to the determined size of the difference between the subgroup of the group of patients and the second subgroup of the group of patients being larger than a selected difference threshold, providing second information (Step 888), the second information may be based on the second statistical query and may be configured to enable a presentation of a graphical illustration of an estimated property of the second subgroup of the group of patients, for example in response to the fourth input from the user; and in response to the determined size of the difference between the subgroup of the group of patients and the second subgroup of the group of patients being smaller than a selected difference threshold, forgoing providing the second information (Step 890). In some implementations, method 880 may comprise one or more additional steps, while some of the steps listed above may be modified or excluded. For example, in some cases Step 882 and/or Step 884 and/or Step 886 and/or Step 888 and/or Step 890 may be excluded from method 880. In some implementations, one or more steps illustrated in FIG. 8F may be executed in a different order and/or one or more groups of steps may be executed simultaneously and/or a plurality of steps may be combined into single step and/or a single step may be broken down to a plurality of steps. In some examples, method 880 and/or Step 882 may be executed after providing the first information by Step 810 of method 800.

In some embodiments, Step 882 may comprise receiving a second subgroup defining input, for example, after providing the first information (for example using Step 810 or Step 834), where the second subgroup defining input may define a second subgroup of the group of patients. In some examples, the second subgroup defining input may be based on an input from a user, such as a third input from the user of method 800. In some examples, Step 882 may receive the second subgroup defining input in a similar fashion to the reception of the subgroup defining input by Step 802 described above. In some examples, the structure of the second subgroup defining input may be similar or identical to the structure of the subgroup defining input of Step 802 described above.

In some embodiments, Step 884 may comprise receiving a second statistical query about the second subgroup of the group of patients defined by the second subgroup defining input of Step 882. In some examples, the second statistical query may be based on an input from a user, such as a fourth input from the user of method 800. In some examples, Step 884 may receive the second statistical query in a similar fashion to the reception of the statistical query by Step 804. In some examples, the structure of the second statistical query may be similar or identical to the structure of the statistical query of Step 804 described above.

In some embodiments, Step 886 may comprise determining a size of a difference between the subgroup of the group of patients defined by the subgroup defining input of Step 802 and the second subgroup of the group of patients defined by the second subgroup defining input of Step 882. For example, Step 886 may determine an exact size of the difference, an estimated size of the difference, and so forth. In one example, Step 886 may determine at least one of the number (and/or a total weight according to an assignment of weight to patients) of patients in the subgroup of the group of patients defined by the subgroup defining input of Step 802 that are not in the second subgroup of the group of patients defined by the second subgroup defining input of Step 882, the number (and/or a total weight according to an assignment of weight to patients) of patients in the second subgroup of the group of patients defined by the second subgroup defining input of Step 882 that are not in the subgroup of the group of patients defined by the subgroup defining input of Step 802, the number (and/or a total weight according to an assignment of weight to patients) of patients that are in both the subgroup of the group of patients defined by the subgroup defining input of Step 802 and the second subgroup of the group of patients defined by the second subgroup defining input of Step 882. Further, in some examples, Step 886 may determine the size of the difference as a linear combination and/or a non-linear combination of one or more of the above determined numbers and/or above determined total weights. In some examples, any function that measures and/or estimates a difference and/or a distance between two mathematical sets may be used by Step 886 to determine the size of the difference.

In some embodiments, Step 888 may comprise providing second information, for example in response to the size of the difference between the subgroup of the group of patients and the second subgroup of the group of patients determined by Step 886 being larger than a selected difference threshold. In some examples, the second information may be based on a statistical query (for example, on the second statistical query received by Step 884). In some examples, the second information may be configured to enable a presentation of a graphical illustration of an estimated property of the second subgroup of the group of patients defined by the second subgroup defining input of Step 882, for example in response to the fourth input from the user of Step 884. For example, Step 888 may provide the second information in a similar fashion to the providence of the first information by Step 810 as described above. In some examples, the second information provided by Step 888 may be identical to the first information of method 800, may be different from the first information of method 800, and so forth.

In some embodiments, Step 890 may comprise forgoing and/or withholding providing the second information of Step 888, for example in response to the size of the difference between the subgroup of the group of patients and the second subgroup of the group of patients determined by Step 886 being smaller than a selected difference threshold.

In some examples, the difference threshold of Step 888 and Step 890 may be selected by method 880. For example, the difference threshold may be read from memory (such as memory units 210, shared memory modules 410, and so forth). In another example, the difference threshold may be received from an external device over a communication network using a communication device (such as communication modules 230, internal communication modules 440, external communication modules 450, and so forth). In yet another example, the difference threshold may be received from a user (for example, through a user interface, through a web page, using an input device, and so forth). In an additional example, the difference threshold may be received as a configuration parameter, for example from a configuration file. In some examples, the difference threshold may be selected based on the selected subgroup size threshold of method 800. For example, in response to a first selected subgroup size threshold of method 800, a first value may be selected for the difference threshold, and in response to a second selected subgroup size threshold of method 800, a second value may be selected for the difference threshold (the second value differs from the first value). In some examples, the difference threshold may be selected in a similar fashion to the selection of the selected subgroup size threshold of method 800 by Step 808 described above. For example, the difference threshold may be randomly selected from a distribution of thresholds. In another example, the difference threshold may be selected based on at least one of whether the subgroup of the group of patients includes a first patient, whether the second subgroup of the group of patients includes a first patient, whether the subgroup of the group of patients includes at least a selected number of patients of a first type (wherein the selected number of patients is one, is two, is between three and five, is above five, and so forth), whether the second subgroup of the group of patients includes at least a selected number of patients of a first type (wherein the selected number of patients is one, is two, is between three and five, is above five, and so forth), the determined size of the subgroup of the group of patients, the size of the second subgroup of the group of patients, the size of the group of patients, a type of the property of the subgroup of the group of patients, a type of the property of the second subgroup of the group of patients, the user, an identity of the user, a type of the user, an identity of a group of at least two users that includes the user, past behavior of the user, at least one previous statistical query that is based on an input from the user, information provided in response to at least one previous statistical query that is based on an input from the user, and so forth.

In some embodiments, a user (such as user 146) may use a computerized data analysis device (such as computerized data analysis device 144) to enter input (such as the first input from the user of Step 802, the second input from the user of Step 804, the third input from the user of Step 882, the fourth input from the user of Step 884, and so forth). The computerized data analysis device may generate a subgroup defining input (such as the subgroup defining input of Step 802, the second subgroup defining input of Step 882, etc.) and/or a statistical query (such as the statistical query received by Step 804, the second statistical query received by Step 884, and so forth) based on the input entered by the user. The computerized data analysis device may provide the generated subgroup defining input and/or statistical query to medical organization 110 (for example, to a computerized device within medical organization 110, to a software of medical organization 110 executed on cloud platform 400, etc.), for example by transmitting the generated subgroup defining input and/or statistical query through communication network 130. Medical organization 110 (for example, using a computerized device, using a software program, etc.)

may use methods 800, 820, 830, 840, 860 and 880 to generate a response to the statistical query including information (such as the first information provided by Step 810 or Step 834, the second information provided by Step 848, Step 868 or Step 888, and so forth), and the generated response may be provided back to computerized data analysis device, for example by transmitting the generated response through communication network 130. Further, in some examples, the computerized data analysis device may receive the generated response, and present a graphical illustration of an estimated property of a subgroup of the group of patients (for example, of an estimated property of the subgroup of the group of patients defined by the subgroup defining input of Step 802, by the second subgroup defining input of Step 882, etc.), for example in response to the input entered by the user (for example, in response to the first input from the user of Step 802, to the second input from the user of Step 804, to the third input from the user of Step 882, to the fourth input from the user of Step 884, and so forth). In some examples, the graphical illustration may be further based on information from public data 120 and/or proprietary medical data 142. In some examples, the graphical illustration may be further based on information received from multiple medical organizations, such as medical organizations 110A, 110B and 110C. For example, each medical organization may provide information as described above, the provided information from the multiple medical organizations may be combined, and the graphical illustration may be based on the combined information.

Figure 9A:
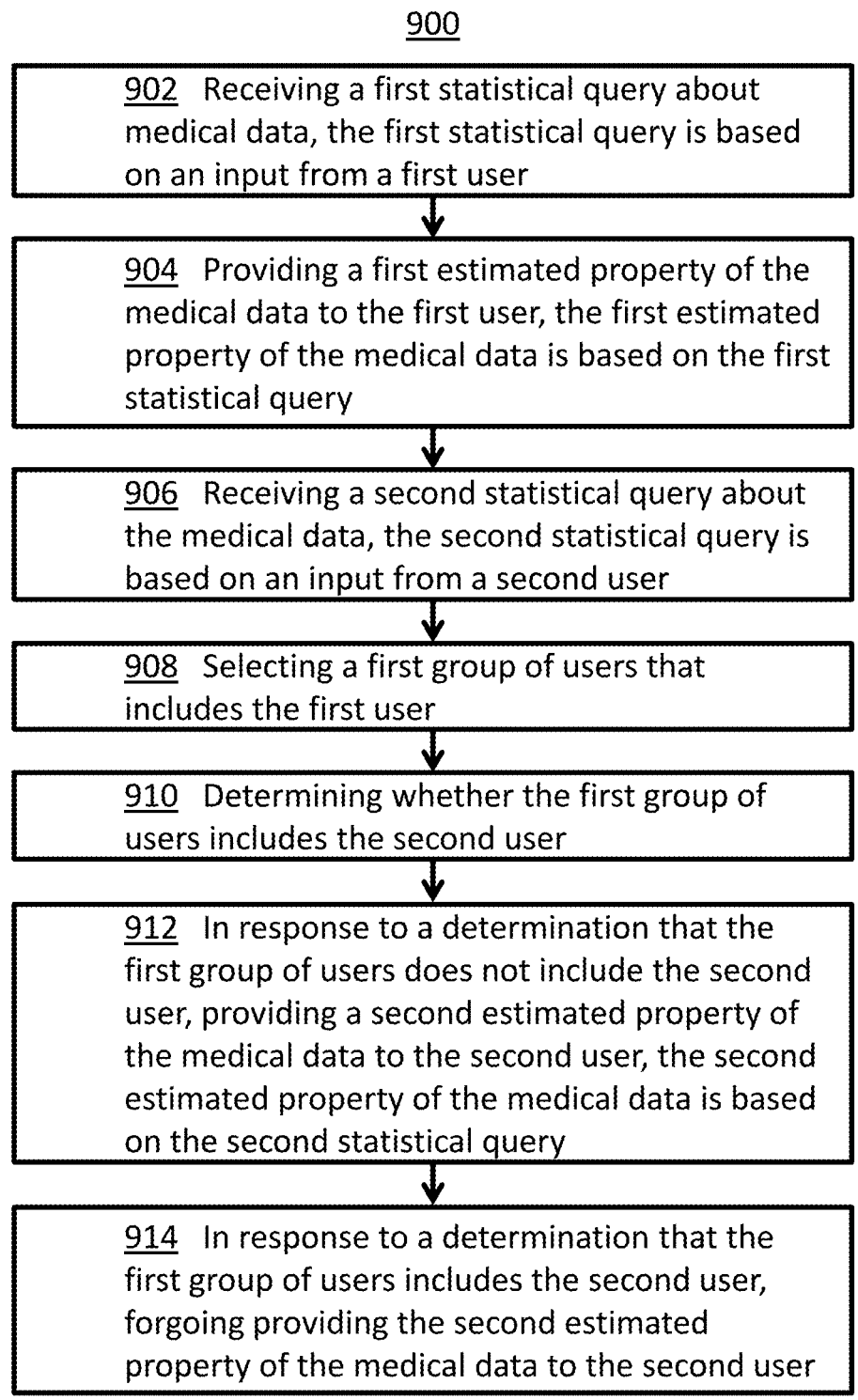
FIG. 9A illustrates an example of a method for selectively providing information about medical data.

FIG. 9A illustrates an example of a method 900 for selectively providing information about medical data. In this example, method 900 may comprise: receiving a first statistical query about medical data (Step 902), the first statistical query may be based on an input from a first user; providing a first estimated property of the medical data to the first user (Step 904), the first estimated property of the medical data may be based on the first statistical query; receiving a second statistical query about the medical data (Step 906), the second statistical query may be based on an input from a second user; selecting a first group of users that includes the first user (Step 908); determining whether the first group of users includes the second user (Step 910); in response to a determination that the first group of users does not include the second user, providing a second estimated property of the medical data to the second user (Step 912), the second estimated property of the medical data may be based on the second statistical query; and in response to a determination that the first group of users includes the second user, forgoing providing the second estimated property of the medical data to the second user (Step 914). In some implementations, method 900 may comprise one or more additional steps, while some of the steps listed above may be modified or excluded. For example, in some cases Step 902 and/or Step 904 and/or Step 906 and/or Step 908 and/or Step 910 and/or Step 912 and/or Step 914 may be excluded from method 900. In some implementations, one or more steps illustrated in FIG. 9A may be executed in a different order and/or one or more groups of steps may be executed simultaneously and/or a plurality of steps may be combined into single step and/or a single step may be broken down to a plurality of steps. In some examples, after completion of Step 912, method 900 may continue to execute method 940. In some examples, after completion of Step 912, method 900 may continue to execute method 960. In some examples, after completion of Step 914, method 900 may continue to execute method 930.

In some embodiments, Step 902 may comprise receiving a first statistical query about medical data. In some examples, the first statistical query received by Step 902 may be based on an input from a first user (such as user 146). In some embodiments, Step 906 may comprise receiving a second statistical query about the medical data. In some examples, the second statistical query received by Step 906 may be based on an input from a second user (such as user 146, user 147, user 148, and so forth). In some examples, the second user may differ from the first user, the second user may be the first user, and so forth. In some embodiments, Step 902 and/or Step 906 may read at least part of the statistical query about the medical data from memory (such as memory units 210, shared memory modules 410, and so forth). In another example, Step 902 and/or Step 906 may receive at least part of the statistical query about the medical data from an external device (such as computerized data analysis device 144, an external device associated with the user, such as a workstation, a mobile device of the user, etc.) over a communication network using a communication device (such as communication modules 230, internal communication modules 440, external communication modules 450, etc.), may receive at least part of the statistical query about the medical data from the user (for example, through a user interface, through a web page, using an input device, through computerized data analysis device 144, etc.), and so forth. In one example, the statistical query about the medical data received by Step 902 and/or the statistical query about the medical data received by Step 906 may include a query in a query language (such as Structured Query Language) that expresses a statistical query about the medical data. In another example, the statistical query about the medical data received by Step 902 and/or the statistical query about the medical data received by Step 906 may include one or more mathematical formulas for calculating a statistical measure of the medical data.

In some embodiments, Step 904 may comprise providing a first estimated property of the medical data, for example to the first user of Step 902. In some examples, the first estimated property of the medical data may be based on a statistical query (for example, on the first statistical query received by Step 902). For example, Step 904 may store the first estimated property of the medical data in memory (such as memory 700, memory units 210, memory modules 410, etc.), in storage device (such as local storage, remote storage, network attached storage, etc.), and so forth. In another example, Step 904 may transmit the first estimated property of the medical data to an external device, for example over a communication network using a communication device (such as communication modules 230, internal communication modules 440, external communication modules 450, and so forth). In some examples, Step 904 may present the first estimated property of the medical data to a user (such as the first user of Step 902), for example through a user interface, through a web page, using an output device (such as a display screen, an augmented reality display system, a printer, a LED indicator, etc.), through computerized data analysis device 144, and so forth. In one example, the first estimated property of the medical data provided by Step 904 may be an actual property of the medical data. In another example, the first estimated property of the medical data provided by Step 904 may be an approximation of an actual property of the medical data.

In some embodiments, Step 908 may comprise selecting a first group of users that includes the first user of Step 902. For example, the first group of users may include any number of users (such as one user, two users, between three and ten users, more than ten users, and so forth). In some examples, Step 908 may select the first group of users of a plurality of alternative groups of users. For example, Step 908 may select the first group of users of a plurality of alternative groups of users based on an identity of the first user of Step 902. In another example, a group of users that maximize a particular criterion function (such as, largest group, smallest group, etc.) from all the groups of users in the plurality of alternative groups of users that includes the first user may be selected. In some examples, the first group of users may be generated, for example by selecting users from a plurality of users according to a user selection rule. In some examples, the first group of users may be selected based on user input. For example, the user may specify the users in the first group of users, may select the first group of users from a plurality of alternative groups, may specify a user selection rule, and so forth. In some examples, the first group of users may be read from memory (such as memory units 210, shared memory modules 410, and so forth). In some examples, a type of the first user of Step 902 may be a particular type, and Step 908 may select the first group of users to include all users of the particular type from a particular plurality of users.

In some embodiments, Step 910 may comprise determining whether the first group of users selected by Step 908 includes the second user of Step 906. For example, a list of the users in the group of users may be accessed to determine whether the second user of Step 906 is in the list, and therefore determine whether the first group of users selected by Step 908 includes the second user of Step 906. In another example, a user selection rule defining which users are in the group of users may be used to determine whether the first group of users selected by Step 908 includes the second user of Step 906.

In some embodiments, Step 912 may comprise providing a second estimated property of the medical data, for example to the second user of Step 906, for example in response to a determination by Step 910 that the first group of users selected by Step 908 does not include the second user of Step 906. In some examples, the second estimated property of the medical data provided by Step 912 and/or Step 934 and/or Step 952 may be based on a statistical query (for example, on the second statistical query received by Step 906). For example, Step 912 and/or Step 934 and/or Step 952 may provide the second estimated property of the medical data in a similar fashion to the providence of the first estimated property of the medical data by Step 904 described above. In one example, the second estimated property of the medical data provided by Step 912 and/or by Step 934 and/or by Step 952 may be an actual property of the medical data. In another example, the second estimated property of the medical data provided by Step 912 and/or by Step 934 and/or by Step 952 may be an approximation of an actual property of the medical data.

In some embodiments, Step 914 may comprise forgoing and/or withholding providing the second estimated property of the medical data of Step 912 to the second user of Step 906, for example in response to a determination by Step 910 that the first group of users selected by Step 908 includes the second user of Step 906.

Additionally or alternatively, in response to a determination that the first group of users includes the second user, Step 914 may cause a suggestion of an alternative statistical query to be provided to the second user of Step 906. In some examples, the alternative statistical query may be based on the second statistical query received by Step 906. For example, Step 914 may select the alternative statistical query from a plurality of possible statistical queries based on the second statistical query received by Step 906. In another example, Step 914 may use a function to transform the second statistical query received by Step 906 into the alternative statistical query. In some examples, Step 914 may provide a suggestion of the alternative statistical query to the second user, may cause an external device (such as computerized data analysis device 144) to provide the alternative statistical query to the second user (for example, by transmitting information configured to cause the external device to provide the alternative statistical query to the second user), and so forth. Further, in some examples, Step 914 may receive an indication that the second user of Step 906 accepted the suggested alternative statistical query. For example, Step 914 may receive user input from the second user indicating that the second user accepted the suggested alternative statistical query, may receive information from an external device (such as computerized data analysis device 144) indicating that the second user accepted the suggested alternative statistical query, and so forth. Further, in some examples, in response to the received indication that the second user accepted the suggested alternative statistical query, Step 914 may provide a third estimated property of the medical data to the second user. For example, the third estimated property of the medical data may be based on the suggested alternative statistical query. For example, Step 914 may provide the third estimated property of the medical data in a similar fashion to the providence of the first estimated property of the medical data by Step 904 described above.

In some embodiments, Step 904 may further comprise updating a privacy budget associated with the first group of users of Step 908 to reflect the providence of the first estimated property of the medical data to the first user of Step 902 by Step 904. For example, a first privacy consumption may be determined based on the first statistical query of Step 902 and/or based on the first estimated property of the medical data, and the privacy budget associated with the first group of users of Step 908 may be updated based on the determined first privacy consumption (for example, by reducing the first privacy consumption from the privacy budget, by multiplying the privacy budget by a factor selected based on the first privacy consumption, and so forth). For example, a machine learning model may be trained using training examples to determine privacy consumption values from queries and/or provided information, and the trained machine learning model may be used to analyze the first statistical query of Step 902 and/or the first estimated property of the medical data to determine the first privacy consumption. An example of such training example may include a record of a query and/or of provided information, together with a label indicating the desired privacy consumption value to be determined.

Further, in some embodiments, Step 910 may further determine whether the updated privacy budget is sufficient for the second statistical query. For example, a projected privacy consumption may be determined based on the first statistical query of Step 906 and/or based on the second estimated property of the medical data to be provided by Step 912 (for example in a similar fashion to the determination of the first privacy consumption described above), and the updated privacy budget may be compared with the determined projected privacy consumption to determine whether the updated privacy budget is sufficient for the second statistical query.

Further, in some embodiments, in response to the determination by Step 910 that the first group of users selected by Step 908 includes the second user of Step 906 and a determination by Step 910 that the updated privacy budget is sufficient for the second statistical query of Step 906, the second estimated property of the medical data may be provided to the second user (for example as described above in relation to Step 912), and in response to the determination by Step 910 that the first group of users selected by Step 908 includes the second user of Step 906 and a determination by Step 910 that the updated privacy budget is insufficient for the second statistical query of Step 906, providing the second estimated property of the medical data to the second user may be withheld and/or forwent.

Further, in some embodiments, after Step 910 determines whether the updated privacy budget is sufficient for the second statistical query, a third statistical query about the medical data may be received. For example, the third statistical query may be based on an additional input from the first user. For example, the third statistical query about the medical data may be received using Step 962. Further, in some examples, in case the first group of users selected by Step 908 includes the second user of Step 906 and the second estimated property of the medical data was not provided to the second user, a third estimated property of the medical data may be provided to the first user (for example, the third estimated property of the medical data may be based on the third statistical query), and in case the first group of users selected by Step 908 includes the second user of Step 906 and the second estimated property of the medical data was provided to the second user, providing the third estimated property of the medical data to the first user may be withheld and/or forwent. For example, the third estimated property of the medical data may be provided in a similar fashion to the providence of the first estimated property of the medical data by Step 904 described above.

Figure 9B:
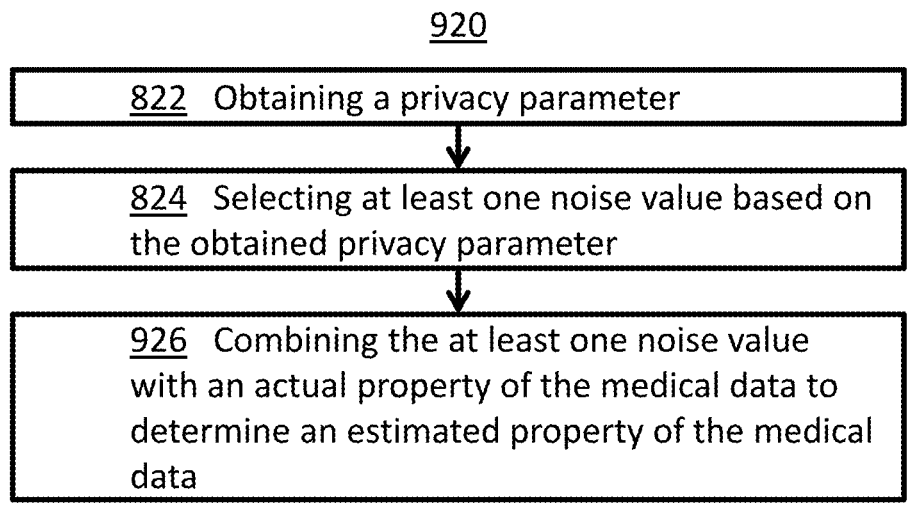
FIG. 9B illustrates an example of a method for determining an estimated property of medical data.

FIG. 9B illustrates an example of a method 920 for determining an estimated property of medical data. In this example, method 920 may comprise: obtaining a privacy parameter (Step 822); selecting at least one noise value based on the obtained privacy parameter (Step 824); and combining the at least one noise value with an actual property of the medical data to determine an estimated property of the medical data (Step 926). In some implementations, method 920 may comprise one or more additional steps, while some of the steps listed above may be modified or excluded. For example, in some cases Step 822 and/or Step 824 and/or Step 926 may be excluded from method 920. In some implementations, one or more steps illustrated in FIG. 9B may be executed in a different order and/or one or more groups of steps may be executed simultaneously and/or a plurality of steps may be combined into single step and/or a single step may be broken down to a plurality of steps.

In some embodiments, Step 926 may comprise combining the at least one noise value selected by Step 824 with an actual property of the medical data to determine an estimated property of the medical data. For example, the actual property of the medical data may include a number, and Step 926 may manipulate the number using a noise value (for example, adding the noise value to the number, multiplying the number by the noise value, etc.) to obtained the estimated property of the medical data. In another example, the actual property of the medical data may include a list of details, and Step 926 may manipulate the list of details using the at least one noise value (for example, dropping at least part of the items in the list of details based on the at least one noise value, adding items to the list of details based on the at least one noise value, modifying items in the list of details based on the at least one noise value, switching the order of the items in the list of details based on the at least one noise value, etc.) to obtained the estimated property of the medical data.

In some embodiments, method 920 may be used one or more times. For example, method 920 may be used at a first time to determine the first estimated property of the medical data of Step 904, may be used at a second time to determine the second estimated property of the medical data of Step 912, and so forth. In some embodiments, Step 822 may obtain a first privacy parameter, Step 824 may select a first at least one noise value based on the first privacy parameter obtained by Step 822, and Step 926 may combine the first at least one noise value selected by Step 824 with a first actual property of the medical data to determine the first estimated property of the medical data of Step 904. Further, in some examples, Step 822 may obtain a second privacy parameter, Step 824 may select a second at least one noise value based on the second privacy parameter obtained by Step 822, and Step 926 may combine the second at least one noise value selected by Step 824 with a second actual property of the medical data to determine the second estimated property of the medical data of Step 912. In one example, the first privacy parameter and the second privacy parameter may be identical. In another example, the first privacy parameter may differ from the second privacy parameter. In one example, the first actual property of the medical data may be identical to the second actual property of the medical data. In another example, the first actual property of the medical data may differ from the second actual property of the medical data. In some examples, in response to the determination by Step 910 that the first group of users selected by Step 908 includes the second user of Step 906 and a first value of the first privacy parameter obtained by Step 822, the second estimated property of the medical data may be provided to the second user (for example in a similar fashion to the providence of the first estimated property of the medical data by Step 904 described above), and in response to the determination by Step 910 that the first group of users selected by Step 908 includes the second user of Step 906 and a second value of the obtained first privacy parameter, providing the second estimated property of the medical data to the second user may be withheld and/or forwent.

Figure 9C:
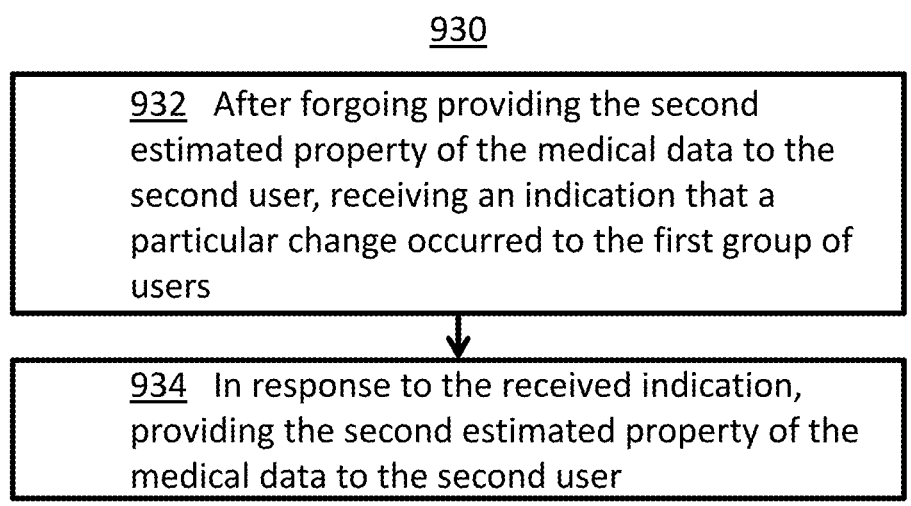
FIG. 9C illustrates an example of a method for selectively providing information about medical data.

FIG. 9C illustrates an example of a method 930 for selectively providing information about medical data. In this example, method 930 may comprise: receiving an indication that a particular change occurred to the first group of users (Step 932), for example after forgoing providing the second estimated property of the medical data to the second user by Step 914; and in response to the received indication, providing the second estimated property of the medical data to the second user (Step 934). In some implementations, method 930 may comprise one or more additional steps, while some of the steps listed above may be modified or excluded. For example, in some cases Step 932 and/or Step 934 may be excluded from method 930. In some implementations, one or more steps illustrated in FIG. 9C may be executed in a different order and/or one or more groups of steps may be executed simultaneously and/or a plurality of steps may be combined into single step and/or a single step may be broken down to a plurality of steps. In some examples, method 930 and/or Step 932 may be executed after forgoing providing the first information by Step 914 of method 900. In some examples, after completion of Step 934, method 930 may continue to execute method 940. In some examples, after completion of Step 934, method 930 may continue to execute method 960.

In some embodiments, Step 932 may comprise receiving, after Step 910 determines that the first group of users includes the second user and/or after Step 914 forgoes providing the second estimated property of the medical data to the second user, an indication that a particular change occurred to the first group of users, for example an indication that the first group of users changed to exclude a particular user, such as the first user of Step 902, the second user of Step 906, a different user, and so forth. For example, Step 932 may receive the indication from a permissions system and/or a permissions database (such as permissions 780), from a repository of regulatory statuses of users, from regulators (such as regulators 650), from a repository of user information, from a repository of employment records (for example, employment records of the user, employment records of medical care providers 630, employment records of insurers 640, employment records of regulators 650, employment records of researchers 660, employment records of facilitators 670, employment records of medical organization 110A, employment records of team 140A, etc.), and so forth. In one example, Step 932 may read the indication from memory (such as memory units 210, shared memory modules 410, and so forth). In another example, Step 932 may receive the indication from an external device over a communication network using a communication device (such as communication modules 230, internal communication modules 440, external communication modules 450, and so forth). In yet another example, Step 932 may receive the indication from a user (for example, through a user interface, through a web page, using an input device, and so forth).

In some embodiments, Step 934 may comprise providing the second estimated property of the medical data to the second user in response to an indication received by Step 932. For example, Step 934 may provide the second estimated property of the medical data to the second user in response to a first indication received by Step 932, and may withhold and/or forgo providing second estimated property of the medical data to the second user in response to a second indication received by Step 932. In another example, Step 934 may provide the second estimated property of the medical data to the second user in response to an indication received by Step 932 that the first group of users changed to exclude one user, and may withhold and/or forgo providing second estimated property of the medical data to the second user in response to an indication received by Step 932 that the first group of users changed to exclude a different user. In one example, Step 934 may comprise providing the second estimated property of the medical data to the second user in response to an indication that the first group of users changed to exclude the second user received by Step 932. In another example, Step 934 may comprise providing the second estimated property of the medical data to the second user in response to an indication that the first group of users changed to exclude the first user received by Step 932.

FIG. 9D illustrates an example of a method 940 for selectively providing information about medical data. In this example, method 940 may comprise: receiving an indication that the first group of users changed to include the second user (Step 942), for example after providing the second estimated property of the medical data to the second user by Step 912 or by Step 934 or by Step 952; and in response to the received indication, providing a notification (Step 944). In some implementations, method 940 may comprise one or more additional steps, while some of the steps listed above may be modified or excluded. For example, in some cases Step 942 and/or Step 944 may be excluded from method 940. In some implementations, one or more steps illustrated in FIG. 9D may be executed in a different order and/or one or more groups of steps may be executed simultaneously and/or a plurality of steps may be combined into single step and/or a single step may be broken down to a plurality of steps. In some examples, method 940 and/or Step 942 may be executed after providing the first information by Step 912 of method 900.

In some embodiments, Step 942 may comprise receiving, after Step 910 determines that the first group of users does not include the second user and/or after Step 912 or Step 934 or Step 952 provide the second estimated property of the medical data to the second user, an indication that the first group of users changed to include the second user. For example, Step 942 may receive the indication from a permissions system and/or a permissions database (such as permissions 780), from a repository of regulatory statuses of users, from regulators (such as regulators 650), from a repository of user information, from a repository of employment records (for example, employment records of the user, employment records of medical care providers 630, employment records of insurers 640, employment records of regulators 650, employment records of researchers 660, employment records of facilitators 670, employment records of medical organization 110A, employment records of team 140A, etc.), and so forth. In one example, Step 942 may read the indication from memory (such as memory units 210, shared memory modules 410, and so forth). In another example, Step 942 may receive the indication from an external device over a communication network using a communication device (such as communication modules 230, internal communication modules 440, external communication modules 450, and so forth). In yet another example, Step 942 may receive the indication from a user (for example, through a user interface, through a web page, using an input device, and so forth).

In some embodiments, Step 944 may comprise providing a notification in response to the providence of the first estimated property of the medical data to the first user by Step 904, and/or to the providence of the second estimated property of the medical data to the second user by Step 912 or Step 934 or Step 952, and/or to the indication received by Step 942 that the first group of users changed to include the second user. In some examples, Step 944 may provide the notification to a user, to a log file, to another process, to an external device, and so forth. For example, Step 944 may store the notification in memory (such as memory 700, memory units 210, memory modules 410, etc.), in storage device (such as local storage, remote storage, network attached storage, etc.), and so forth. In another example, Step 944 may transmit the notification to an external device, for example over a communication network using a communication device (such as communication modules 230, internal communication modules 440, external communication modules 450, and so forth). In some examples, Step 944 may present the notification to a user, for example through a user interface, through a web page, using an output device (such as a display screen, an augmented reality display system, a printer, a LED indicator, etc.), through computerized data analysis device 144, and so forth.

FIG. 9E illustrates an example of a method 950 for selectively providing information about medical data. In this example, method 950 may comprise: in response to the second statistical query of Step 906 belonging to a selected group of statistical queries and the determination by Step 910 that the first group of users of Step 908 includes the second user of Step 906, providing the second estimated property of the medical data to the second user (Step 952); and in response to the second statistical query of Step 906 not belonging to the selected group of statistical queries and the determination by Step 910 that the first group of users of Step 908 includes the second user of Step 906, forgoing providing the second estimated property of the medical data to the second user (Step 954). In some implementations, method 950 may comprise one or more additional steps, while some of the steps listed above may be modified or excluded. For example, in some cases Step 952 and/or Step 954 may be excluded from method 950. In some implementations, one or more steps illustrated in FIG. 9E may be executed in a different order and/or one or more groups of steps may be executed simultaneously and/or a plurality of steps may be combined into single step and/or a single step may be broken down to a plurality of steps. In some examples, method 950 may be executed after Step 910 of method 900, for example instead of Steps 914 of method 900. In some examples, after completion of Step 952, method 950 may continue to execute method 940. In some examples, after completion of Step 952, method 950 may continue to execute method 960.

In one example, the selected group of statistical queries of method 950 may include a query about a total number of patients in the medical data, may exclude a query about a number of patients that match a particular criterion, and so forth. In some examples, the selected group of statistical queries of method 950 may include a query about a statistic of a particular property in the medical data of patients in a first group of patients when the size of the first group of patients is above a selected threshold, and may exclude the query about the statistic of the particular property in the medical data of patients in the first group of patients when the size of the first group of patients is below the selected threshold. For example, the selected threshold may be based on the particular property. In another example, the selected threshold may be based on the second user of Step 906.

In some embodiments, Step 952 may comprise providing the second estimated property of the medical data of Step 912, for example to the second user of Step 906, for example in response to the second statistical query of Step 906 belonging to a selected group of statistical queries and/or to the determination by Step 910 that the first group of users of Step 908 includes the second user of Step 906.

In some embodiments, Step 954 may comprise forgoing providing the second estimated property of the medical data of Step 912 to the second user of Step 906 in response to the second statistical query of Step 906 not belonging to the selected group of statistical queries and/or the determination by Step 910 that the first group of users of Step 908 includes the second user of Step 906.

FIG. 9F illustrates an example of a method 960 for selectively providing information about medical data. In some examples, method 960 as well as all individual steps therein may be performed after Step 910 determined that the first group of users does not include the second user and/or after Step 912 or by Step 934 or by Step 952 provided the second estimated property of the medical data to the second user. In this example, method 960 may comprise: receiving a third statistical query about the medical data (Step 962), the third statistical query may based on an additional input from the first user of Step 902; determining whether the first group of users selected by Step 908 changed to include the second user of Step 906 (Step 964); in response to a determination that the first group of users did not change to include the second user, providing a third estimated property of the medical data to the first user of Step 902 (Step 966), the third estimated property of the medical data may be based on the third statistical query; and in response to a determination that the first group of users changed to include the second user, forgoing providing the third estimated property of the medical data to the first user (Step 968). In some implementations, method 960 may comprise one or more additional steps, while some of the steps listed above may be modified or excluded. For example, in some cases Step 962 and/or Step 964 and/or Step 966 and/or Step 968 may be excluded from method 960. In some implementations, one or more steps illustrated in FIG. 9F may be executed in a different order and/or one or more groups of steps may be executed simultaneously and/or a plurality of steps may be combined into single step and/or a single step may be broken down to a plurality of steps.

In some embodiments, Step 962 may comprise receiving a third statistical query about the medical data, for example after Step 910 determined that the first group of users does not include the second user and/or after Step 912 or by Step 934 or by Step 952 provided the second estimated property of the medical data to the second user. For example, the third statistical query is based on an additional input from the first user. For example, Step 962 may receive the third statistical query about the medical data in a similar fashion to the reception of the first statistical query about the medical data by Step 902 described above.

In some embodiments, Step 964 may comprise determining whether the first group of users selected by Step 908 changed to include the second user of Step 906, for example after Step 910 determined that the first group of users does not include the second user and/or after Step 912 or by Step 934 or by Step 952 provided the second estimated property of the medical data to the second user. For an indication that the first group of users selected by Step 908 changed to include the second user of Step 906 may be received by Step 942 as described above, in response to such received indication, Step 964 may determine that the first group of users selected by Step 908 changed to include the second user of Step 906, and in response to a lack of such indication, Step 964 may determine that the first group of users selected by Step 908 did not change to include the second user of Step 906.

In some embodiments, Step 966 may comprise providing a third estimated property of the medical data to the first user of Step 902, for example in response to a determination by Step 964 that the first group of users selected by Step 908 did not change to include the second user of Step 906. For example, the third estimated property of the medical data may be based on the third statistical query. In some examples, Step 966 may provide the third estimated property of the medical data in a similar fashion to the providence of the first estimated property of the medical data by Step 904 described above.

In some embodiments, Step 968 may comprise forgoing providing the third estimated property of the medical data of Step 966 to the first user of Step 902, for example in response to a determination by Step 964 that the first group of users selected by Step 908 changed to include the second user of Step 906.

It will also be understood that the system according to the invention may be a suitably programmed computer, the computer including at least a processing unit and a memory unit. For example, the computer program can be loaded onto the memory unit and can be executed by the processing unit. Likewise, the invention contemplates a software program being readable by a computer for executing the method of the invention. The invention further contemplates a non-transitory computer readable medium storing a software program comprising data and/or computer implementable instruction for currying out any one or more of the methods described above.

What is claimed is:

1. A non-transitory computer readable medium storing a software program comprising data and computer implementable instructions for carrying out a method for selectively providing information about medical data, the method comprising:
  receiving a first statistical query about medical data, the first statistical query is based on an input from a first user;
  providing a first estimated property of the medical data to the first user, the first estimated property of the medical data is based on the first statistical query;
  receiving a second statistical query about the medical data, the second statistical query is based on an input from a second user, the second user differs from the first user;
  selecting a first group of users that includes the first user;
  determining whether the first group of users includes the second user;
  in response to a determination that the first group of users does not include the second user, providing a second estimated property of the medical data to the second user, the second estimated property of the medical data is based on the second statistical query; and
  in response to a determination that the first group of users includes the second user, forgoing providing the second estimated property of the medical data to the second user.

2. The non-transitory computer readable medium of claim 1, wherein the method further comprises:
  obtaining a first privacy parameter;
  selecting a first at least one noise value based on the first obtained privacy parameter;
  combining the first at least one noise value with a first actual property of the medical data to determine the first estimated property of the medical data;
  obtaining a second privacy parameter;
  selecting a second at least one noise value based on the second obtained privacy parameter; and
  combining the second at least one noise value with a second actual property of the medical data to determine the second estimated property of the medical data.

3. The non-transitory computer readable medium of claim 2, wherein the method further comprises:
  in response to the determination that the first group of users includes the second user and a first value of the obtained first privacy parameter, providing the second estimated property of the medical data to the second user; and
  in response to the determination that the first group of users includes the second user and a second value of the obtained first privacy parameter, forgoing providing the second estimated property of the medical data to the second user.

4. The non-transitory computer readable medium of claim 1, wherein the first estimated property of the medical data is a first actual property of the medical data.

5. The non-transitory computer readable medium of claim 1, wherein the method further comprises:
  updating a privacy budget associated with the first group of users to reflect the providence of the first estimated property of the medical data to the first user;
  determining whether the updated privacy budget is sufficient for the second statistical query;
  in response to the determination that the first group of users includes the second user and a determination that the updated privacy budget is sufficient for the second statistical query, providing the second estimated property of the medical data to the second user; and
  in response to the determination that the first group of users includes the second user and a determination that the updated privacy budget is insufficient for the second statistical query, forgoing providing the second estimated property of the medical data to the second user.

6. The non-transitory computer readable medium of claim 5, wherein the method further comprises:
  after determining whether the updated privacy budget is sufficient for the second statistical query, receiving a third statistical query about the medical data, the third statistical query is based on an additional input from the first user;
  in case the first group of users includes the second user and the second estimated property of the medical data was not provided to the second user, providing a third estimated property of the medical data to the first user, the third estimated property of the medical data is based on the third statistical query; and
  in case the first group of users includes the second user and the second estimated property of the medical data was provided to the second user, forgoing providing the third estimated property of the medical data to the first user.

7. The non-transitory computer readable medium of claim 1, wherein the method further comprises, after determining that the first group of users does not include the second user and providing the second estimated property of the medical data to the second user:
  receiving a third statistical query about the medical data, the third statistical query is based on an additional input from the first user;
  determining whether the first group of users changed to include the second user;
  in response to a determination that the first group of users did not change to include the second user, providing a third estimated property of the medical data to the first user, the third estimated property of the medical data is based on the third statistical query; and
  in response to a determination that the first group of users changed to include the second user, forgoing providing the third estimated property of the medical data to the first user.

8. The non-transitory computer readable medium of claim 1, wherein the method further comprises:
  after determining that the first group of users includes the second user and forgoing providing the second estimated property of the medical data to the second user, receiving an indication that the first group of users changed to exclude the second user; and
  in response to the received indication that the first group of users changed to exclude the second user, providing the second estimated property of the medical data to the second user.

9. The non-transitory computer readable medium of claim 1, wherein the method further comprises:
  after determining that the first group of users includes the second user and forgoing providing the second estimated property of the medical data to the second user, receiving an indication that the first group of users changed to exclude the first user; and in response to the received indication that the first group of users changed to exclude the first user, providing the second estimated property of the medical data to the second user.

10. The non-transitory computer readable medium of claim 1, wherein the method further comprises:
   after determining that the first group of users does not include the second user and providing the second estimated property of the medical data to the second user, receiving an indication that the first group of users changed to include the second user; and
   in response to the providence of the first estimated property of the medical data to the first user, the providence of the second estimated property of the medical data to the second user, and the received indication that the first group of users changed to include the second user, providing a notification.

11. The non-transitory computer readable medium of claim 1, wherein the method further comprises:
   in response to the second statistical query belonging to a selected group of statistical queries and the determination that the first group of users includes the second user, providing the second estimated property of the medical data to the second user; and
   in response to the second statistical query not belonging to the selected group of statistical queries and the determination that the first group of users includes the second user, forgoing providing the second estimated property of the medical data to the second user.

12. The non-transitory computer readable medium of claim 11, wherein the selected group of statistical queries includes a query about a total number of patients in the medical data and does not include a query about a number of patients that match a particular criterion.

13. The non-transitory computer readable medium of claim 11, wherein the selected group of statistical queries includes a query about a statistic of a particular property in the medical data of patients in a first group of patients when the size of the first group of patients is above a selected threshold, and does not include the query about the statistic of the particular property in the medical data of patients in the first group of patients when the size of the first group of patients is below the selected threshold.

14. The non-transitory computer readable medium of claim 13, wherein the selected threshold is based on the particular property.

15. The non-transitory computer readable medium of claim 13, wherein the selected threshold is based on the second user.

16. The non-transitory computer readable medium of claim 1, wherein the method further comprises:
   in response to a determination that the first group of users includes the second user, causing a suggestion of an alternative statistical query to be provided to the second user, the alternative statistical query is based on the second statistical query;
   receiving an indication that the second user accepted the suggested alternative statistical query; and
   in response to the received indication that the second user accepted the suggested alternative statistical query, providing a third estimated property of the medical data to the second user, the third estimated property of the medical data is based on the suggested alternative statistical query.

17. The non-transitory computer readable medium of claim 1, wherein the method further comprises selecting the first group of users of a plurality of alternative groups of users based on an identity of the first user.

18. The non-transitory computer readable medium of claim 1, wherein a type of the first user is a particular type, and the selected first group of users includes all users of the particular type from a particular plurality of users.

19. A system for selectively providing information about medical data, the system comprising:
   at least one processing device configured to:
      receive a first statistical query about medical data, the first statistical query is based on an input from a first user;
      provide a first estimated property of the medical data to the first user, the first estimated property of the medical data is based on the first statistical query;
      receive a second statistical query about the medical data, the second statistical query is based on an input from a second user, the second user differs from the first user;
      select a first group of users that includes the first user;
      determine whether the first group of users includes the second user;
      in response to a determination that the first group of users does not include the second user, provide a second estimated property of the medical data to the second user, the second estimated property of the medical data is based on the second statistical query; and
      in response to a determination that the first group of users includes the second user, forgo providing the second estimated property of the medical data to the second user.

20. A method for selectively providing information about medical data, the method comprising:
   receiving, at a computing device, a first statistical query about medical data, the first statistical query is based on an input from a first user;
   providing a first estimated property of the medical data to the first user, the first estimated property of the medical data is based on the first statistical query;
   receiving a second statistical query about the medical data, the second statistical query is based on an input from a second user, the second user differs from the first user;
   selecting a first group of users that includes the first user;
   determining whether the first group of users includes the second user;
   in response to a determination that the first group of users does not include the second user, providing a second estimated property of the medical data to the second user, the second estimated property of the medical data is based on the second statistical query; and
   in response to a determination that the first group of users includes the second user, forgoing providing the second estimated property of the medical data to the second user.

* * * * *